(12) United States Patent
Birkbeck et al.

(10) Patent No.: US 9,095,448 B2
(45) Date of Patent: Aug. 4, 2015

(54) METHOD OF USING AN ALIGNMENT GUIDE

(75) Inventors: Alec Birkbeck, Leeds (GB); Robert Freeman, Leeds (GB); Gary Moore, Leeds (GB); Steven Gowers, Leeds (GB)

(73) Assignee: DEPUY INTERNATIONAL LIMITED (GB)

( * ) Notice: Subject to any disclaimer, the term of this patent is extended or adjusted under 35 U.S.C. 154(b) by 769 days.

(21) Appl. No.: 12/773,557

(22) Filed: May 4, 2010

(65) Prior Publication Data

US 2011/0276053 A1    Nov. 10, 2011

(51) Int. Cl.
  *A61B 17/56* (2006.01)
  *A61F 2/46* (2006.01)

(52) U.S. Cl.
  CPC ....... *A61F 2/4609* (2013.01); *A61F 2002/4668* (2013.01); *A61F 2002/4687* (2013.01)

(58) Field of Classification Search
  CPC ........... A61F 2/4609; A61F 2002/4687; A61F 2002/4668
  USPC ........................................ 606/86 R–91, 99
  See application file for complete search history.

(56) References Cited

U.S. PATENT DOCUMENTS

| | | | | |
|---|---|---|---|---|
| 1,942,640 A | * | 1/1934 | Fromme | 81/177.9 |
| 2,379,796 A | * | 7/1945 | Freeman et al. | 188/196 BA |
| 4,716,894 A | * | 1/1988 | Lazzeri et al. | 606/91 |
| 5,061,270 A | * | 10/1991 | Aboczky | 606/91 |
| D331,461 S | * | 12/1992 | Lester | D24/140 |
| 5,250,051 A | * | 10/1993 | Maryan | 606/91 |
| 5,284,483 A | * | 2/1994 | Johnson et al. | 606/86 R |
| 5,320,625 A | * | 6/1994 | Bertin | 606/91 |
| 5,364,403 A | * | 11/1994 | Petersen et al. | 606/91 |
| 5,457,857 A | * | 10/1995 | Lam | 24/503 |
| 5,540,697 A | * | 7/1996 | Rehmann et al. | 606/91 |

(Continued)

FOREIGN PATENT DOCUMENTS

| | | | |
|---|---|---|---|
| DE | 10202582 C1 * | 9/2003 | ............. A61B 19/00 |
| EP | 1920713 A2 | 5/2008 | |

(Continued)

OTHER PUBLICATIONS

DePuy International Ltd. Pinnacle Acetabular Cup System Surgical Technique; Cat. No. 9068-80-050; Leeds, England, 2003.

(Continued)

*Primary Examiner* — Matthew Lawson
*Assistant Examiner* — Zade Coley

(57) ABSTRACT

A method of aligning an alignment guide relative to a reamed acetabulum of a patient is provided. The method includes the step of manipulating an alignment guide comprising a shaft having a longitudinal axis and a guide arm having a first portion, a second portion and a third portion, the first portion attached to the shaft and configured to be rotatable about a first axis substantially perpendicular to the longitudinal axis, the second portion extending from the first portion at a first predetermined angle along a second axis, and the third portion extending from the second portion at a second predetermined angle. The guide arm is rotated about the first axis relative to the shaft. A cup or trial is attached to the distal end of the shaft and positioned to contact the reamed acetabulum. The third portion of the guide arm is then oriented with respect to the long axis of the patient and the surface of the table on which the patient is positioned.

19 Claims, 14 Drawing Sheets

(56) References Cited

U.S. PATENT DOCUMENTS

| | | | |
|---|---|---|---|
| 5,584,837 A * | 12/1996 | Petersen | 606/91 |
| 5,658,294 A * | 8/1997 | Sederholm | 606/91 |
| 5,683,399 A * | 11/1997 | Jones | 606/91 |
| 6,395,005 B1 * | 5/2002 | Lovell | 606/91 |
| 6,743,235 B2 * | 6/2004 | Subba Rao | 606/91 |
| 7,037,310 B2 * | 5/2006 | Murphy | 606/91 |
| 2002/0125756 A1 * | 9/2002 | Asano | 297/367 |
| 2005/0107799 A1 * | 5/2005 | Graf et al. | 606/91 |

FOREIGN PATENT DOCUMENTS

| | | |
|---|---|---|
| WO | WO 0130247 A1 | 5/2001 |
| WO | WO 03057087 A2 | 7/2003 |
| WO | WO 2004030556 A2 | 4/2004 |
| WO | WO 2010128320 A1 | 11/2010 |
| WO | WO 2010145769 A1 | 12/2010 |
| WO | WO 2011095804 A1 | 8/2011 |

OTHER PUBLICATIONS

DePuy International Ltd. Pinnacle Acetabular Cup System Surgical Technique; Cat. No. 0611-42-050 (Rev. 3); Aug. 24, 2004; USA.

DePuy International Ltd. Pinnacle Acetabular Cup System Surgical Technique; Cat. No. 9068-80-050 version 2; Jun. 2009; Leeds, England.

Langston,D.J., et al.; The Effect of Component Size and Orientation on the Concentrations of Metal Ions After Resurfacing Arthroplasty of the Hip; The Journal of Bone & Joint Surgery, pp. 1143-1152, vol. 90-B, No. 9, Sep. 2008, England.

Murray, D.W.; The Definition and Measurement of Acetabular Orientation; The Journal of Bone and Joint Surgery, pp. 228-232, vol. 75•B, No. 2, Mar. 1993, England.

* cited by examiner

FIG. 1
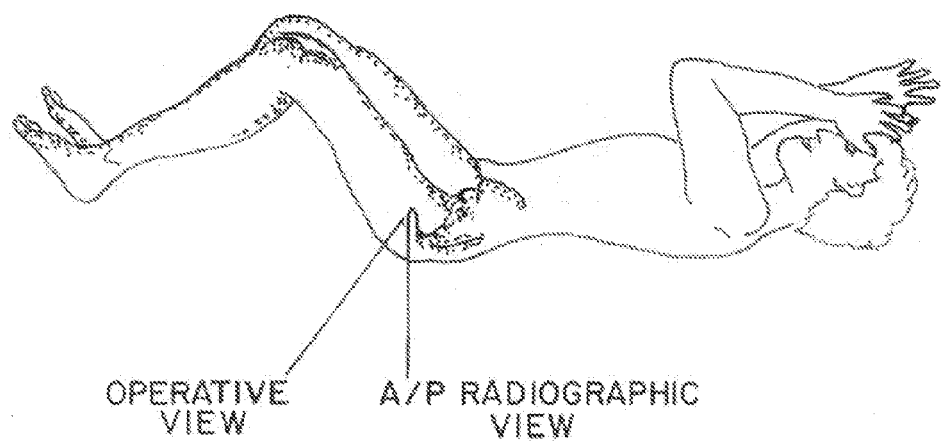
OPERATIVE VIEW    A/P RADIOGRAPHIC VIEW
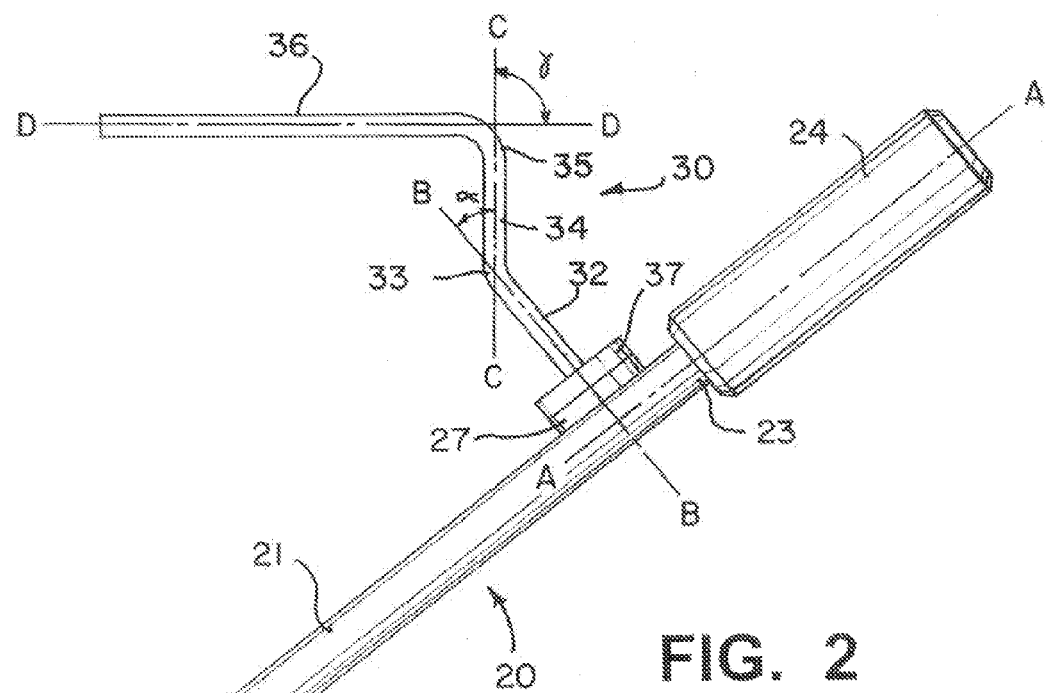
FIG. 2

METHOD OF USING AN ALIGNMENT GUIDE

The present invention relates to an alignment guide. In particular, the present invention relates to an alignment guide for aligning an instrument, more particularly an alignment guide for use with the implantation of a hip cup.

BACKGROUND OF THE INVENTION

Hip replacement surgery typically is performed to compensate for severe damage of the acetabulum due to disease, trauma or other factors, and includes the steps of removing all or part of the existing joint and substituting for the removed bone a femoral component attached to the patient's femur and an acetabular cup attached to the patient's acetabulum. The prosthetic acetabular cup is implanted to substitute for the socket of the hip joint, and is mated with a prosthetic femoral component to complete the hip replacement surgery. In order to achieve optimal performance of the combined acetabular and femoral prostheses, the acetabular cup must be properly positioned in the acetabulum. An improperly positioned acetabular component can lead to dislocations of the hip joint, decreased range of motion, and eventual loosening or failure of one or both of the acetabular and femoral components.

Acetabular cups may be formed of a metal, ceramic or plastic. Incorrect acetabular component positioning can lead to edge loading and undesirable effects across bearings composed of any material, such as dislocation, increased wear, ceramic squeaking, elevated metal ion release and fractures. Studies of post-operative cup placement demonstrate that seating the cup in particular orientations provides for improved wear patterns compared with seating the cup in other orientations. For example, a study by Langton et al., entitled "The Effect of Component Size and Orientation on the Concentrations of Metal Ions after Resurfacing Arthroplasty of the Hip", and published in the Journal of Bone Joint Surgery (2008; 90-B:1143-51) demonstrates that the version angle (as measured on EBRA software) may influence wear. To improve the wear of the cup and the product performance of the hip system, a surgeon endeavours to seat the cup in an orientation that is predicted to provide good wear patterns in accordance with the post-operative studies.

In preparation for surgery, the patient is x-rayed in the same two planes as those provided for in the post-operative studies. The surgeon then uses the x-rays as a means of preliminarily planning the size of the acetabular and femoral prostheses and the position of each when surgery is complete. During surgery, the surgeon uses a reamer to remove bone to form a hemispherical shape in the acetabulum. The reamed acetabulum enables a nearly unlimited number of angular cup positions as the cup may be seated at any angle within the hemisphere.

Next, the surgeon attaches the cup to an inserter/impactor and attempts to position the cup in a way that approximates the planned-for angles in the pre-operative plan. Surgeons often have difficulty in performing this step as he or she must manipulate the cup in three dimensions while attempting to correct for angular changes that occur when translating the pre-operative radiographic angle into operative angles. Thus, a common cause of malpositioning is the difference between the radiographic angles provided in the pre-operative plan and the operative angles observed by the surgeon.

FIG. 1 depicts the difference in the projection of angles seen from different views. For example, 45° of inclination and 30° of anteversion achieved in the operative environment will provide a steeper inclination angle of 50° when displayed on an A/P radiograph. To achieve a position that will provide a 45° inclination angle on the A/P radiograph, the surgeon must adjust the operative inclination angle. Thus, to succeed in positioning the cup at a desired angle, the surgeon needs to translate the information from the post-operative studies generated in two dimensions at a first viewing angle into data that is useful when in the operating theatre, where the surgeon operates in three dimensions and observes the patient at a viewing angle that is not the viewing angle provided in an A/P radiograph.

To assist surgeons in accurately locating and aligning prostheses and instruments, surgeons commonly rely on instruments. Inclination and version guides are widely used during total hip arthroplasty to assist in aligning the acetabular cup. Separate guides may be provided for inclination and version angle. Alternatively, a combined guide may be provided. One known form of combined alignment guide enables the position of the acetabular cup to be set at an angle relative to the floor of the operating room and the long axis of the patient. Such an alignment guide (that provides a measure of operative angles to position the cup inserter in surgery) does not directly represent what the surgeon will see post-operatively on an A/P radiograph. As discussed earlier, all of the clinical analysis on cup wear has been based on post-operative measurements. As a result, the surgeon aims to position the cup to match as closely as possible the desired position as shown in a post-operative radiograph of the cup. The disadvantage of using operative angles in surgery is that, as you vary operative anteversion, the radiographic inclination angle of the cup changes.

It is an object of embodiments of the present invention to obviate or mitigate one or more of the problems associated with the prior art, whether identified herein or elsewhere.

BRIEF SUMMARY OF THE INVENTION

The present invention provides an alignment guide that accounts for changes in inclination when the user adjusts the version angle so as to more accurately position the cup inserter in surgery. Further, an embodiment of the alignment guide can be designed such that adjustment of inclination and version angles are made independently of each other.

According to a first aspect of the present invention there is provided an alignment guide that includes a shaft having a longitudinal axis; a housing configured to be attached to the shaft and being rotatable about a first axis substantially perpendicular to the longitudinal axis; a guide arm having a first portion and a second portion, the first portion being attached to the housing and extending from the housing along a second axis, the second portion extending from the first portion at a first predetermined angle.

According to a second aspect of the present invention there is provided an alignment guide that includes a shaft having a longitudinal axis; a guide arm having a first portion, a second portion and a third portion, the first portion being attached to the shaft and configured to be rotatable about a first axis substantially perpendicular to the longitudinal axis, the second portion extending from the first portion at a first predetermined angle along a second axis, the third portion extending from the second portion at a second predetermined angle.

According to a third aspect of the present invention there is provided an alignment guide that includes a shaft having a longitudinal axis; a housing configured to be attached to the shaft; a guide arm having a first portion, a second portion and third portion, the first portion configured to be at least partially received in the housing and extending from the housing along a first axis that is substantially perpendicular to the longitudinal axis, the second portion extends from the first portion at a first predetermined angle, the third portion extends from second portion at a second predetermined angle, the guide arm configured to be rotatable about the first axis.

According to another aspect of the present invention there is provided a method of using the alignment guide to position a cup or trial in a patient's acetabulum. The method is for aligning an alignment guide relative to a reamed acetabulum of a patient having a long axis positioned on an operating table, and includes the steps of:

manipulating an alignment guide comprising a shaft having a longitudinal axis; a guide arm having a first portion, a second portion and a third portion, the first portion being attached to the shaft and configured to be rotatable about a first axis substantially perpendicular to the longitudinal axis, the second portion extending from the first portion at a first predetermined angle along a second axis, and the third portion extending from the second portion at a second predetermined angle; and a cup or trial attached to the distal end of the shaft;

attaching the guide arm to the shaft;

rotating the guide arm about the first axis relative to the shaft;

contacting the cup or trial with the reamed acetabulum; and while maintaining contact between the cup or trial and the reamed acetabulum, adjusting the position of the alignment guide such that the third portion of the guide arm is substantially parallel to the operating table when viewed from the side of the table and is substantially parallel to the long axis of the patient.

The present invention will now be described, by way of example only, with reference to the accompanying drawings, in which:

BRIEF DESCRIPTION OF THE DRAWINGS

FIG. 1 is a plan view illustrating the operative and A/P radiographic viewing angles of a patient lying in a lateral decubitus position ready for surgery;

FIG. 2 is a side elevational view of an alignment guide in accordance with a first embodiment of the present invention;

DETAILED DESCRIPTION OF THE INVENTION

Figure 3:
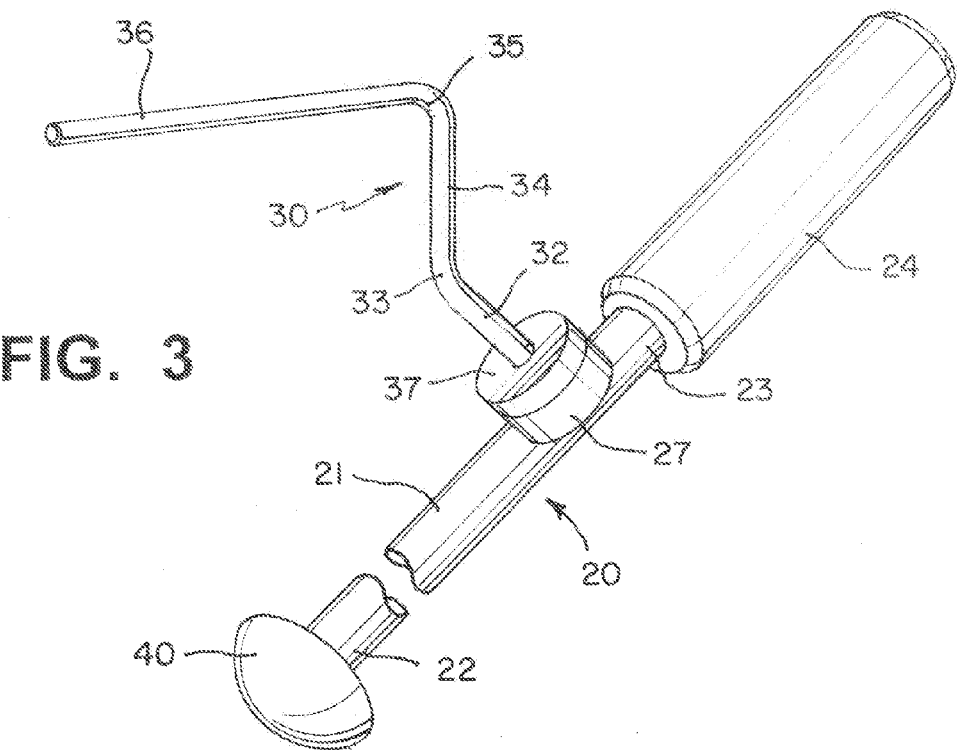
FIG. 3 is a perspective view of an alignment guide in accordance with the embodiment of FIG. 2.

Referring to FIGS. 2 and 3, a first embodiment of the alignment guide is generally referenced as reference numeral 20. Alignment guide 20 includes a shaft 21 having a longitudinal axis A and a guide arm, generally referenced as reference numeral 30, releasably attached to shaft 21. Alignment guide 20 may be attached to a cup or trial 40 at distal end 22 of shaft 21. Alignment guide 20 may include a handle 24 attached at proximal end 23 of shaft 21. Guide arm 30 may be attached to shaft 21 such that shaft 21 and guide arm 30 are co-planar in a first position. Guide arm 30 is preferably configured such that guide arm 30 may be detached from shaft 21, rotated to a second position about a first axis B substantially perpendicular to the longitudinal axis A at which position guide arm 30 is out of plane with shaft 21, and then re-attached to shaft 21. Alternatively, guide arm 30 may be spring biased with respect to shaft 21 such that a user could apply a force to overcome the spring bias to separate guide arm from shaft 21 to rotate guide arm 30 and shaft 21 with respect to one another.

Guide arm 30 includes a first portion 32, a second portion 34 and a third portion 36. Preferably, first portion 32, second portion 34 and third portion 36 of guide arm 30 are co-planar. First portion 32 is attachable to shaft 21 and is rotatable about a first axis B that is substantially perpendicular to longitudinal axis A. Second portion 34 may be attached at the distal end of first portion 32 or at some point along the length of first portion 32. Second portion 34 extends from first portion 32 at a first predetermined angle α along a second axis C. In a preferred embodiment, first predetermined angle α ranges from 30 to 50 degrees, and more preferably approximately 40 degrees. In a preferred embodiment, the distal end of first portion 32 transitions smoothly to second portion 34 at transition 33. Third portion 36 may be attached at the distal end of second portion 34 or at some point along the length of first portion 34. In a preferred embodiment, the distal end of second portion 34 transitions smoothly to third portion 36 at transition 35. Third portion 36 extends from second portion 34 at a second predetermined angle γ along a third axis D. In a preferred embodiment, second predetermined angle γ is approximately 90 degrees.

Figure 4:
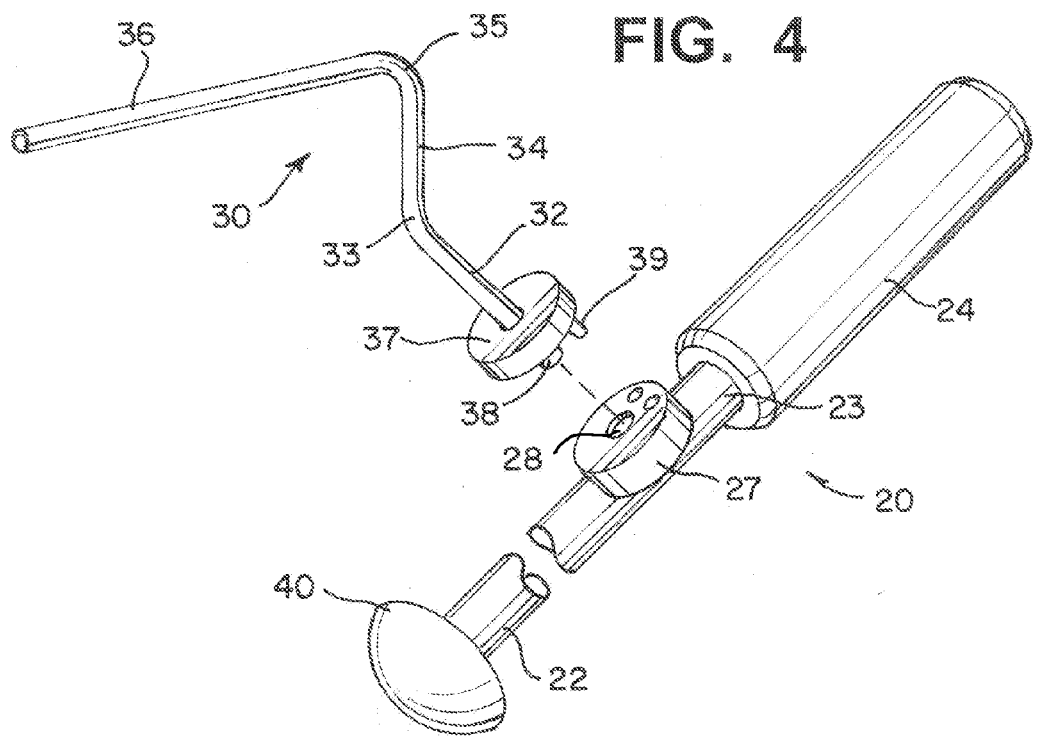
FIG. 4 is a perspective view of an alignment guide in accordance with the embodiment of FIG. 2, wherein the guide arm is shown separated from the shaft.

Shaft 21 may include a base 27 that extends from a surface of shaft 21 in a direction generally perpendicular to longitudinal axis A. It is understood that base 27 can be formed in shaft 21 or be a separate component that is attached to shaft 21, in which case base 27 may be glued or welded to shaft 21, for example. Referring to FIG. 4, base 27 has a first recess 28 and at least two slots 29a, 29b. In a preferred embodiment, first portion 32 of guide arm 30 includes a cover 37 that has a protrusion 38 sized and shaped to be at least partially received within recess 28, and a tab 39 sized and shaped to be at least partially received within each of the at least two slots 29a, 29b. In this way, cover 37 and base 27 are configured to be attached to one another in more than one orientation. Cover 37 can be detached from base 27 and mated with base 27 such that protrusion 38 is disposed within recess 28 and tab 39 is disposed within slot 29a. If the surgeon chooses, cover 37 can be detached from base 27, rotated with respect to axis B, and then mated with base 27 such that protrusion 38 is disposed within recess 28 and tab 39 is disposed within slot 29b. Base 27 can be cylindrical in shape and first recess 28 can be located centrally to facilitate rotation of guide arm 30. Protrusion 38 can extend further from cover 37 than tab 39 such that at least a portion of protrusion 38 is disposed within recess 28 when the user disengages tab 39 from slots 29a, 29b to facilitate rotation and the mating of recesses and tabs.

While FIG. 4 depicts two slots 29a, 29b, it is understood that base 27 could include a plurality of slots 29 that are spaced apart at predetermined intervals such that guide arm 30 can be rotated about axis B with respect to shaft 21 at known angular increments. In this way, because guide arm 30 is attached to cover 37, guide arm 30 may be attached to shaft 21 in a position where guide arm 30 is coplanar with longitudinal axis A of shaft 21 or out of plane with respect to shaft 21 by the angular increment that guide arm 30 was rotated with respect to shaft 21. In a preferred embodiment, up to fifteen slots could be provided at increments of three to ten degrees, but most preferably five degree increments. As one skilled in the art will understand, base 27 and cover 37 can be configured to attach in other ways. For example, base 27 can have a protrusion that extends from an upper surface that is configured to be received in a recess in cover 37. Similarly, base 27 can include a tab that extends upwardly that is configured to be received within slots formed in cover 37. Alternatively, cover 37 and base 27 can have a combination of tabs and slots, and/or protrusions and recesses that enable a user to attach cover 37 and base 27 to one another at two or more positions. The tab and slot features could be located on the perimeter of base 27 and cover 37 and/or could communicate with the perimeter of base 27 and cover 37 and/or be located within the perimeter of the body of one or the other or both base 27 and cover 37. Protrusion 38 may be spring biased with respect to base 27 by attaching a spring (not shown) to protrusion 38 (or cover 37) and base 27. In this way, a user could apply a force to overcome the spring bias to separate cover 37 from base 27 a distance that disengages tab 39 from slots 29 and permits cover 37 to be rotated with respect to base 27.

In each of the embodiments described herein, shaft 21 may be attachable directly to cup or trial 40 or attachable to a separate component that is itself attachable to cup or trial 40. The separate component need not be aligned with longitudinal axis A along its entire length, but preferably attaches to cup or trial 40 at a point that is collinear with longitudinal axis A or at least parallel to longitudinal axis A. Thus, shaft 21 may be a short shaft that is attachable to an inserter shaft that is attachable to cup or trial 40. Alternatively, shaft 21 may have a proximal portion that defines longitudinal axis A and a distal portion that is curved and/or has at least two lengths that are not parallel to longitudinal axis A.

Figure 5:
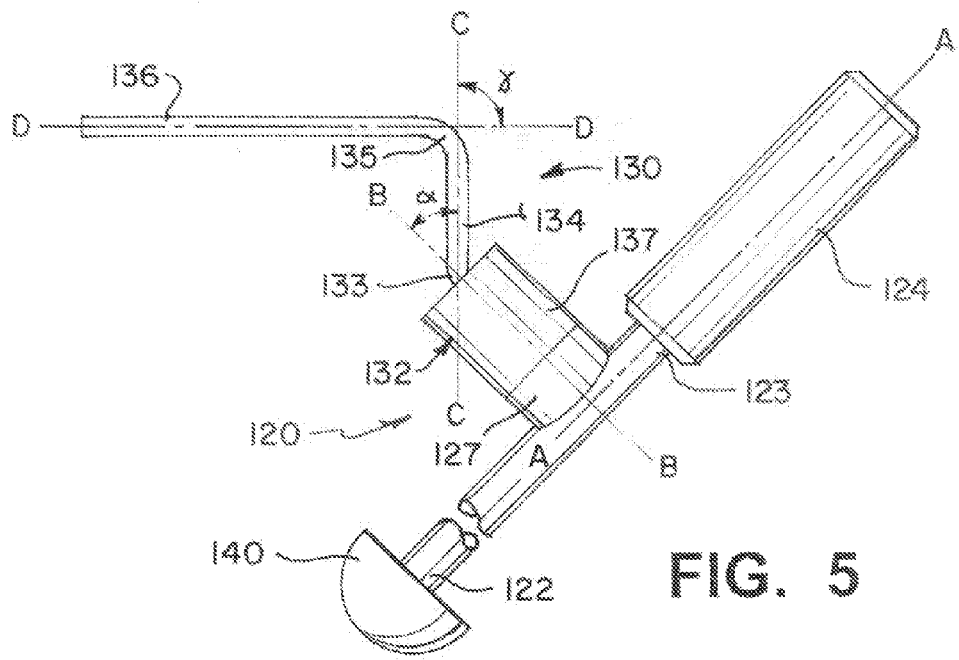
FIG. 5 is a side elevational view of an alignment guide in accordance with a second embodiment of the present invention.

Referring to FIG. 5, a second embodiment of an alignment guide 120 is depicted. Similar structures are labelled similarly to the corresponding structures of the first embodiment. Alignment guide 120 includes a shaft 121 having a longitudinal axis A, and a guide arm, generally indicated as reference numeral 130, releasably attached to shaft 121. Alignment guide 120 may be attached to a cup or trial 140 at distal end 122 of shaft 121. Alignment guide 120 may include a handle 124 attached at proximal end 123 of shaft 121. Guide arm 130 may be attached to shaft 121 such that shaft 121 and guide arm 130 are co-planar in a first position. Guide arm 130 is preferably configured such that guide arm 130 may be rotated to a second position about a first axis B substantially perpendicular to the longitudinal axis A at which position guide arm 130 is out of plane with shaft 121.

Guide arm 130 includes a housing 132 that is attached to shaft 121, a first portion 134 attached to housing 132, and a second portion 136 attached to first portion 134. Housing 132 includes a base 127 attached to shaft 121, and a cover 137 rotatable relative to base 127 about first axis B. First portion 134 extends from housing 132 along a second axis C at a first predetermined angle α. Second portion 136 extends from first portion 134 at a second predetermined angle γ. In a preferred embodiment, second predetermined angle γ is approximately 90 degrees. As with the first embodiment, first portion 34 may be attached at the distal end of housing 132 or at some point along the length of housing 132. First portion 134 may attach directly to housing 132 or attach to housing 132 via a linking portion 133 that transitions from first portion 134 to housing 132. Linking portion 133 may transition from axis C to axis B along a straight or curved line. Second portion 136 may be attached at the distal end of first portion 134 or at some point along the length of first portion 134. In a preferred embodiment, the distal end of first portion 134 transitions smoothly to second portion 136 at transition 135. Base 127 and cover 137 may be configured to be lockable with respect to one another.

As with the first embodiment, base 127 extends from a surface of shaft 121 in a direction generally perpendicular to longitudinal axis A. Base 127 can be formed in shaft 121 or be a separate component that is attached to shaft 121. Base 127 may be glued or welded to shaft 21, for example. As with the embodiment depicted in FIG. 4, cover 137 and base 127 may have a combination of features, such as slots/recesses and protrusions/tab, to permit cover 137 and base 127 to be attached to one another at different angular positions relative to longitudinal axis A. It is understood that each of the different combinations of mating features described with respect to the first embodiment may be employed to attach or mate cover 137 and base 127. Because guide arm 130 is attached to cover 137, guide arm 130 may be attached to shaft 21 in a position where guide arm 30 is coplanar with longitudinal axis A of shaft 121 or out of plane with respect to longitudinal axis A of shaft 21 by the angular increment that guide arm 30 was rotated with respect to shaft 21. As with the first embodiment, the angular increments can be provided in known increments of, for instance, three to ten degrees, but most preferably five degree increments.

Referring to Referring to FIGS. 6-9, a third embodiment of an alignment guide 220 is depicted. Similar structures are labelled similarly to the corresponding structures of the prior embodiments. Alignment guide 220 includes a shaft 221 having a longitudinal axis A, and a guide arm, generally indicated as reference numeral 230, releasably attached and rotatably attached to shaft 221. Alignment guide 220 may be attached to a cup or trial (not shown) at distal end 222 of shaft 221. Alignment guide 120 may include a handle 224 attached at proximal end 223 of shaft 221. Guide arm 230 may be attached to shaft 221 such that shaft 221 and guide arm 230 are co-planar in a first position. Guide arm 230 is preferably configured such that guide arm 230 may be rotated to a second position about a first axis B substantially perpendicular to the longitudinal axis A at which position guide arm 230 is out of plane with shaft 221. Preferably, guide arm 230 is rotatable in angular increments with respect to shaft 221. As with the first two embodiments, the angular increments can be provided in known increments of, for instance, three to ten degrees, but most preferably five degree increments.

Guide arm 230 includes a first portion 232, a second portion 234 and a third portion 236. Second portion 234 may be attached at the distal end of first portion 232 or at some point along the length of first portion 232. In a preferred embodiment, the distal end of first portion 232 transitions smoothly to second portion 234. Third portion 236 may be attached at the distal end of second portion 234 or at some point along the length of first portion 234. In a preferred embodiment, the distal end of second portion 234 transitions smoothly to third portion 236. Second portion 234 extends from first portion 232 at a first predetermined angle α along a second axis C. In a preferred embodiment, first predetermined angle α ranges from 30 to 50 degrees, and more preferably approximately 40 degrees. Third portion 236 extends from second portion 234 at a second predetermined angle γ along a third axis D. In a preferred embodiment, second predetermined angle γ is approximately 90 degrees.

Figure 6:
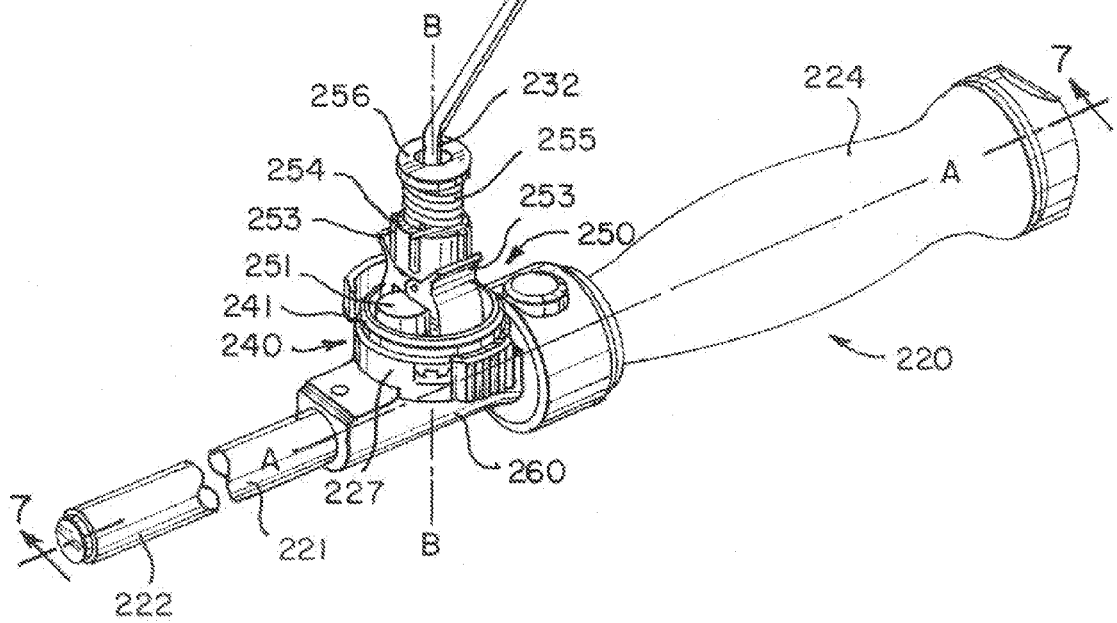
FIG. 6 is a perspective view of an alignment guide in accordance with a third embodiment of the present invention the alignment guide.
Figure 7:
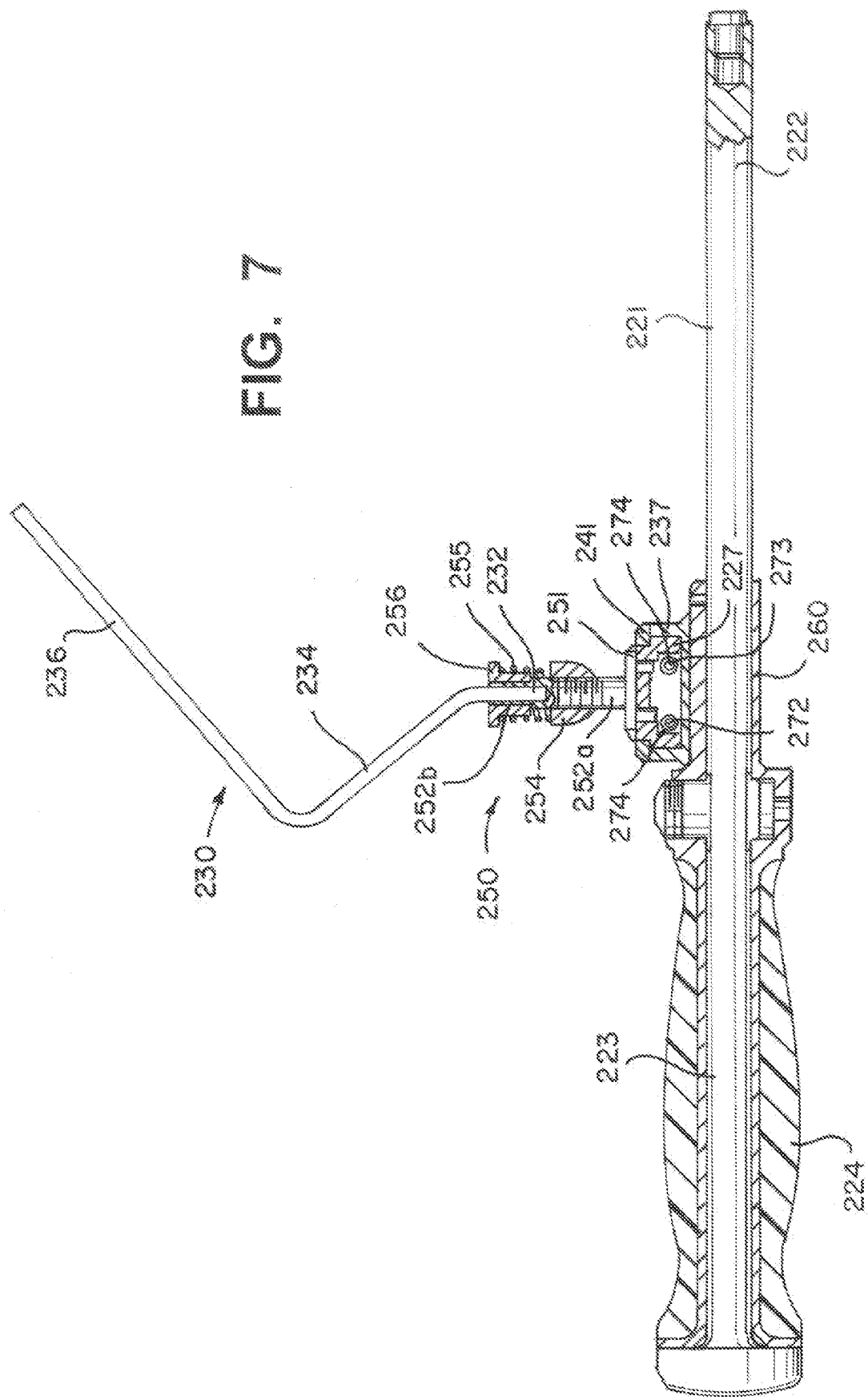
FIG. 7 is a side cross-sectional view of the alignment guide of FIG. 6 taken along lines 7-7 of FIG. 6.
Figure 8:
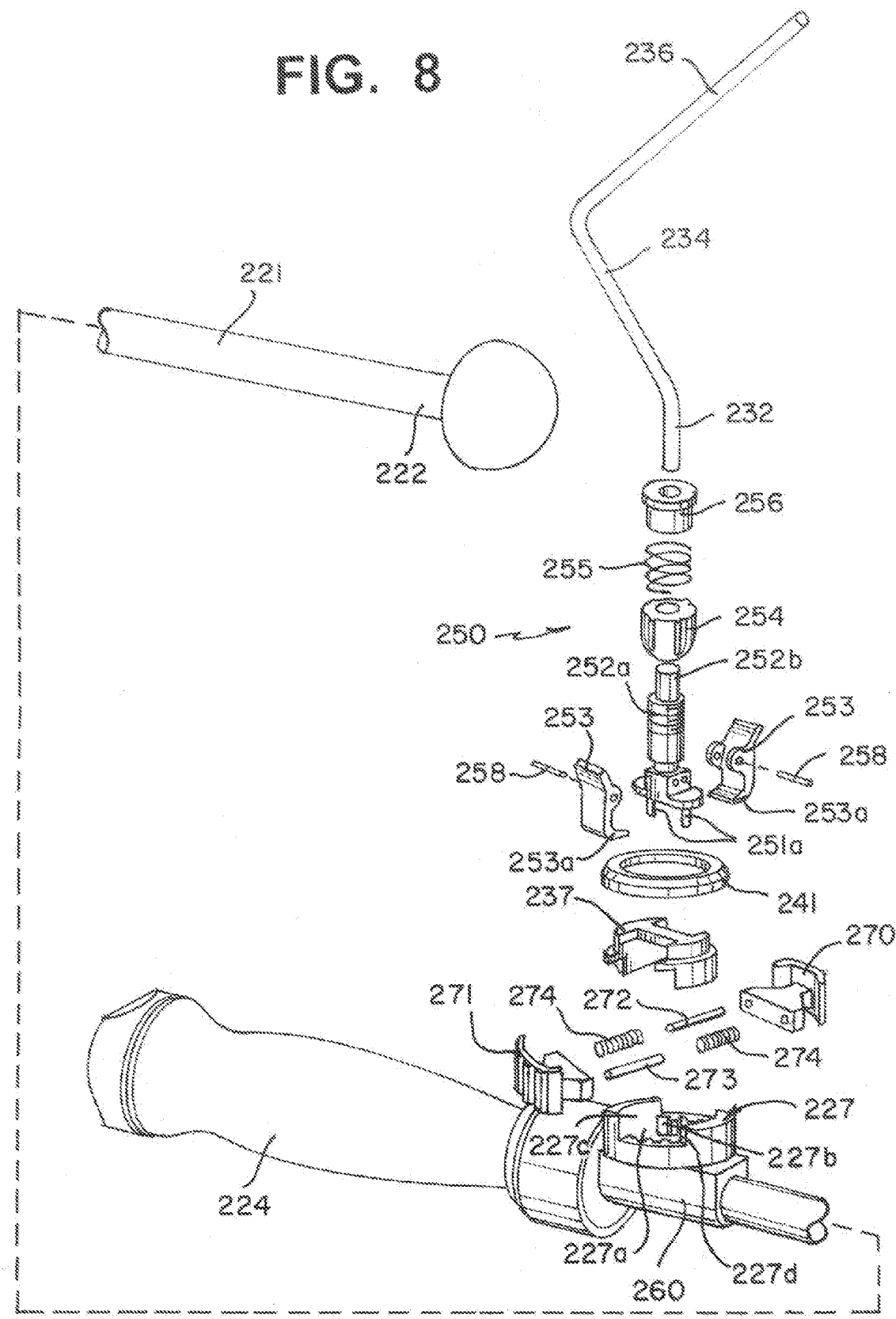
FIG. 8 is an exploded perspective view of the alignment guide of FIG. 6.

The third embodiment differs from the first two embodiments in that the mechanisms for detachably attaching guide arm 230 to shaft 221 and rotating guide arm 230 with respect to shaft 221 are more complex. As shown in FIGS. 6-8, guide arm 230 is attached to a clip 250 which is adapted to be releasably attached to a housing 240, which in turn is attached to shaft 221. Housing 240 includes a base 227 attached to shaft 221 and a cap 241 attached to an upper portion of base 227. A bezel 237 is rotatably attached to base 227 about a first axis B, which is substantially perpendicular to longitudinal axis A. Bezel 237 is preferably captured within housing 240 between base 227 and cap 241, and is configured to be rotatable with respect to base 127 and lockable with respect to base 127 at discrete positions.

Base 227 of housing 240 is mounted or attached to shaft 221. In the embodiment depicted in FIGS. 6 and 7, shaft 221 is circular in cross-section (though shaft 221 may have any cross-sectional shape), and includes a platform 260 formed on a proximal portion of shaft 221. Platform 260 preferably has a generally rectilinear cross-section and one side that is flat so as to more readily attach base 227 to that side. Base 227 may be attached to platform 260 (or directly to shaft 221) in any manner known to one skilled in the art, but one in which permits no relative movement between base 227 and shaft 221. For example, depending upon the material of base 227, it may be glued or welded to platform 260.

Preferably base 227 includes a ring 227a that has an inner surface with teeth 227b formed thereon over at least a segment of the inner surface. Ring 227a is preferably centered on first axis B. Preferably, teeth 227b are formed on a lower portion of the inner surface of ring 227a. Ring 227a includes a first portion 227c and a second portion 227d of increased height as measured from the platform 261. The first portion 227c and second portion 227d preferably are opposed from one another and extend approximately between 60 and 110 degrees about base 227, but most preferably approximately 90 degrees. Cap 241 is attached to first portion 227c and second portion 227d such that windows 228 are formed between cap 241 and ring 227a. Preferably the windows extend over at least that portion of ring 227a that includes teeth 227b. Ring 227a also includes a shoulder 227e formed above teeth 227b about the inner circumference of ring 227a.

As described above, bezel 237 is rotatably attached to base 227 about first axis B. Bezel 237 has two opposed arcuate portions 237a connected by a central bar 237b. The arcuate portions each have a lower surface 237e dimensioned to contact shoulder 227e of base 227, and an outer arcuate surface 237c dimensioned to contact the inner surface of first and second portions 227c, 227d. When disposed within housing 240, bezel 237 is thus captured between cap 241 and base 227 and is freely rotatable with respect to base 227. Arcuate portions 237a each may have a reduced diameter portion 237d that together with outer surface 237c form a shoulder 237E Shoulder 237f thus provides clearance for cap 241 to be attached to first portion 227c and second portion 227d and permits bezel 237 to freely rotate between cap 241 and base 227.

Figure 9:
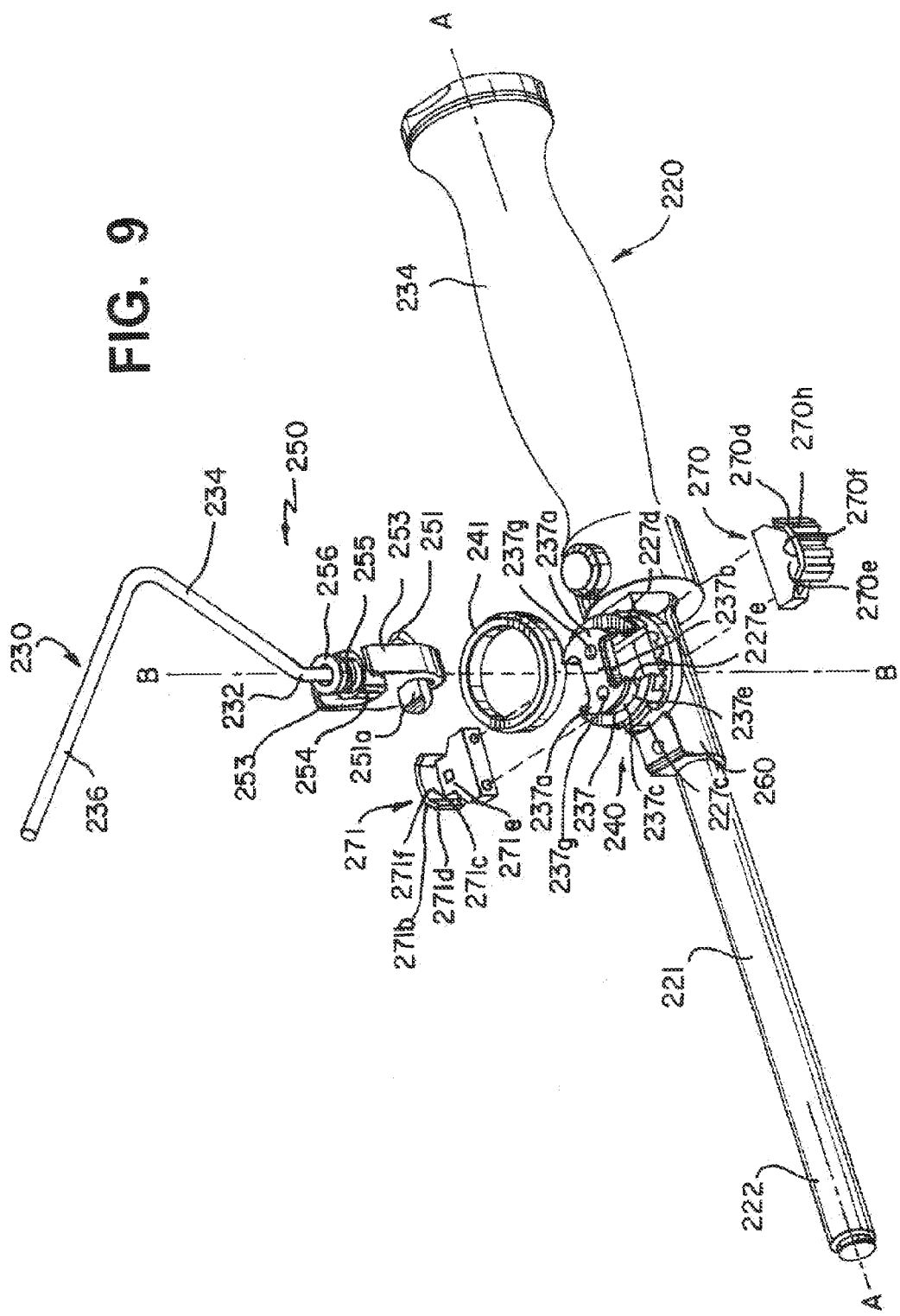
FIG. 9 is an partially exploded perspective view of the alignment guide of FIG. 6, having ratchet springs and pins omitted for clarity.

Referring to FIGS. 7 and 9, cap 241 preferably has an opening to permit clip 250 to extend through cap 241 and be releasably attached to bezel 237. Bezel 237 may have one or more guideholes 237g in a top surface to guide the user when clip 250 is attached to bezel 237. Preferably, guideholes 237g are configured to permit clip 250 to attach to bezel only in a single orientation.

Housing 240 is configured to receive therein a first male ratchet member 270 and a second male ratchet member 271. Male ratchet members 270, 271 are captured within base 227 and cap 241 so as to be rotatable with respect to the base 227 within window 228. First male ratchet member 270 has a first opening 270a and a second opening 270b, spaced apart from first opening 270a, formed in an inner surface of first male ratchet member 270. Similarly, second male ratchet member 271 has a first opening 271a and a second opening 271b, spaced apart from first opening 271a, formed in an inner surface of second male ratchet member 271. One of the male ratchet member 270 and second male ratchet member 271 is configured to receive a first end of a first ratchet pin 272 and a second ratchet pin 273 in openings 270a, 270b or 271a, 271b. The other of the male ratchet member 270 and second male ratchet member 271 is configured to receive one end each of a pair of ratchet springs 274 in openings 270a, 270b or 271a, 271b. The other end of ratchet springs 274 are received on the second end of first ratchet pin 272 and a second ratchet pin 273. Ratchet pins 270, 271 are attached to bezel 237.

Referring more particularly to FIG. 9, first male ratchet member 270 and second male ratchet member 271 each have an inner portion 270c, 271c and an outer portion 270d, 271d and an arm 270e, 271e connect that connects the inner portions to the outer portions. Arms 270e, 271e are dimensioned to extend through window 228 formed between base 227 and cap 241, and accommodate the thickness of ring 227a. Each outer portion 270d, 271d extends substantially perpendicularly from the arm and has a height that is greater than the height of window 228. Each outer portion 270d, 271d has an outer grip surface 270h, 271h and an inner surface 270f, 271f that preferably is shaped such that as the respective ratchet member is moved about the base and cap, inner surfaces 270f, 271f are not impeded by the base or cap. Preferably, the inner surface of the outer portions are arcuate and defines an arc of a circle that is slightly larger than that defined by the base or cap.

Inner portions 270c, 271c of ratchet members 270, 271 are configured to closely mate with bezel 237 when ratchet members 270c, 271c are assembled within housing 240 such that when the ratchet members are rotated, bezel 237 also rotates. Ratchet members 270, 271 are formed with at least one ratchet tooth 270g, 271g (see FIG. 10A) on the respective outer surfaces of the inner portions 270c, 271c. Each of the ratchet teeth 270g, 271g are disposed between inner portions 270c, 271c and outer portions the 270d, 271d and below arms 270c, 271c. Ratchet teeth 270g, 271g are shaped to engage the teeth 227b of base 227 or the space defined therebetween. When assembled within housing 240, ratchet teeth 270g, 271g of male ratchet members 270, 271 are spring biased to engage teeth 227b of base 227. A user may impart a compressive force on the opposed grip surfaces 270h, 271h of ratchet members, which acts against springs 274, which serves to reduce the distance between the distal end of ratchet teeth 270g, 271g such that ratchet teeth 270c, 271c disengage from base teeth 227b.

In this way, bezel 237, which is directly connected to ratchet members 270, 271, may then be rotated with respect to base 227. Teeth 227b and ratchet teeth 270c, 271c are configured such that rotating bezel 237 angularly by one tooth will adjust the bezel 237 by a known angular increment, which in turn adjusts guide arm 230 (which is directly attached to bezel 237) by the same angular amount. Preferably, each base tooth is spaced apart from a next tooth by approximately three to ten degrees, but most preferably five degrees.

Figure 11:
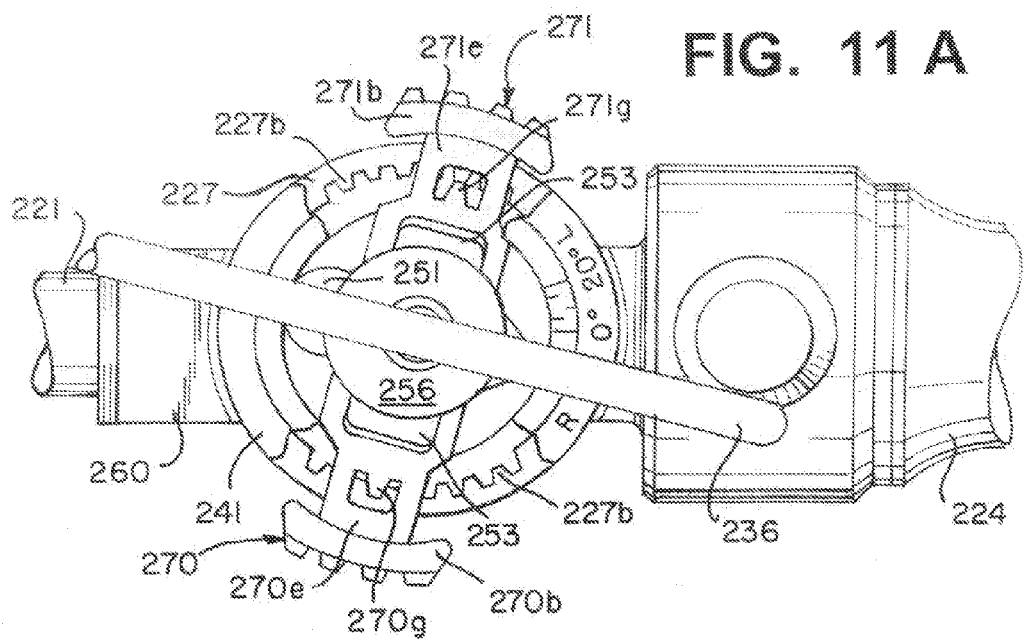
FIGS. 11A, 11B and 11C are, respectively, a top plan, bottom plan and perspective view of the alignment guide of FIG. 6 at a second position, wherein the guide arm is not co-planar with the shaft.
Figure 11:
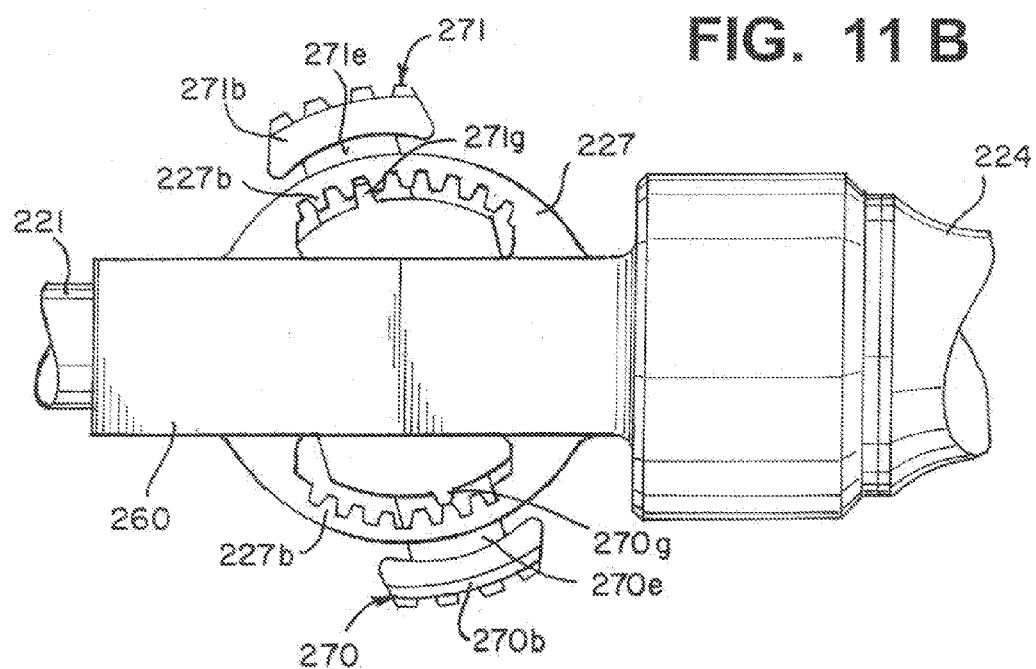
Figure 11:
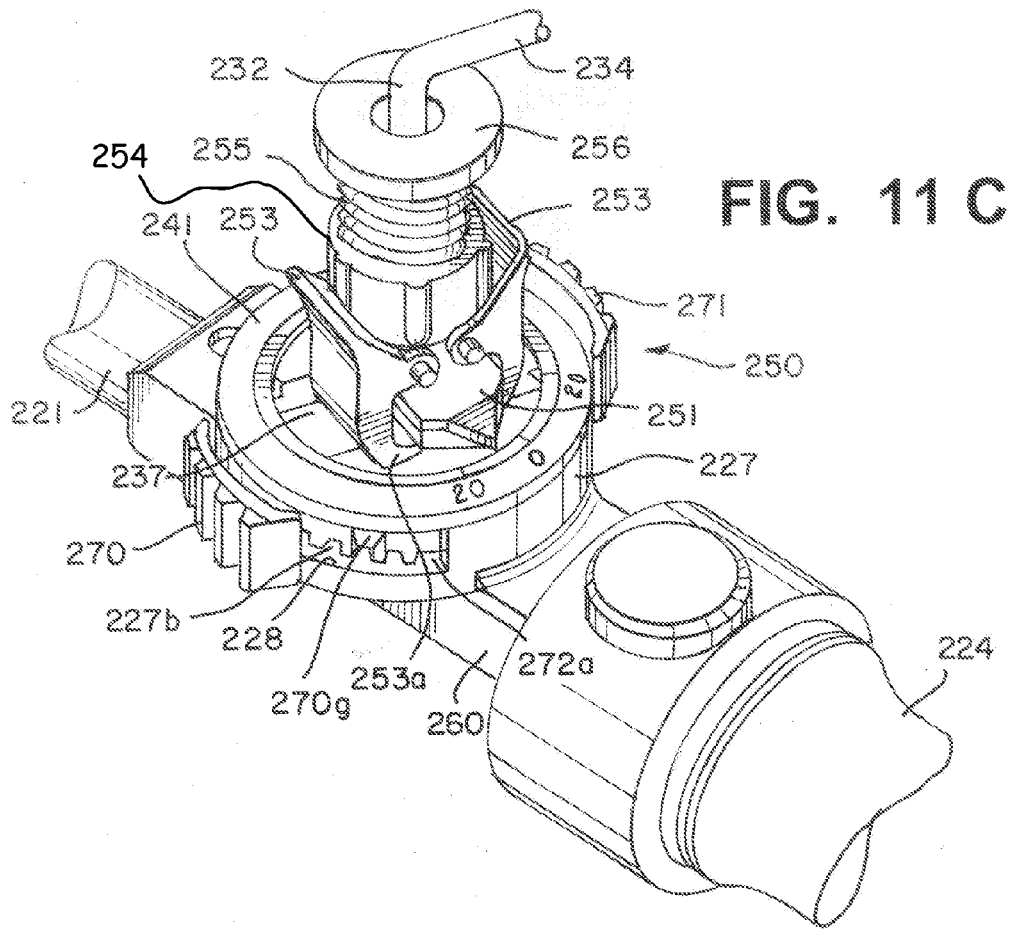

Referring to FIG. 11C, cap 241 may have indicia printed thereon to indicate the amount of anteversion guide arm 230 will provide when bezel 237 is rotated relative to base 227 and shaft 221. Preferably, the indicia would include a "0" marking aligned with longitudinal axis A, and have tick or numeric markings indicating the degree of anteversion on either side of the "0" marking provided when guide arm 230 is rotated in either direction. Alignment guide 220 is designed to be used on either the left or right leg. Hence, the measurement of anteversion depends on which leg the alignment guide is being used.

Referring to FIG. 8, as described above, clip 250 serves to releasably attach guide arm 230 to housing 240 and more particularly, bezel 237. In a preferred embodiment, clip 250 includes a locking plate 251, a post 252 extending from a top surface thereof, and at least two stakes 251a extending from a bottom surface thereof. Stakes 251a are dimensioned and spaced such that they may be received within guide holes 237g of bezel 237. In a preferred embodiment, one of stakes 251a is configured to mate with a first guide hole 237g and the other of stakes 251a is configured to mate with a second guide hole 237g such that plate 251 mates with bezel 237 in only one orientation. That is, the mating components 251a and 237g are configured such that each of the two different stakes 251a is shaped and/or sized to fit in only one of each of the two different guideholes 237g. As shown in FIG. 11C, locking plate 251 can include an indicator on a top surface that points to the tick or numeric markings on cap 241 when clip 250 is assembled with bezel 237.

Post 252 includes a lower portion 252a that extends from a top surface of locking plate 251 and a upper portion 252b that extends from lower portion 252a. A shoulder 252c is formed where the cross-sectional dimension of upper portion 252b steps down from the cross-sectional dimension of lower portion 252a. At least a portion of lower portion 252a is threaded to receive a lock nut 254. A lock-nut spring 255 is disposed about upper portion 252b between lock nut 254 and a spring cap 256. Spring cap 256 has a centrally located bore for receiving the distal end of first portion 232 of guide arm 230. The bore of spring cap 256 is configured to communicate with a similar bore in upper portion 252b of post 252. Each of the bores is dimensioned to receive at least a portion of first portion 232 of guide arm 230.

Clip 250 includes a pair of levers 253 pivotably connected on opposing sides of lower portion 252a of post 252. Levers 253 each have a pair of ears that are dimensioned to be disposed about one side of post 252. Each of the pair of ears has a pinhole that communicates with a throughhole that passes through opposing sides of lower portion 252a when levers 253 are engaged with post 252. A pin disposed through the pair of ears of levers 253 and the throughhole of post 252 pivotably connects each of levers 253 to post 252. Levers 253 each have a lower lip 253a that engages at least the sides and preferably the underside of central bar 237b when levers 253 are in a first position at which point lock nut 254 is screwed down onto lower portion 252a of post 252.

When lock nut 254 is positioned distally on lower portion 252a, lock nut 254 contacts an upper surface of levers 253 to prevent levers 253 from rotating with respect to each other thereby preventing lips 253a from disengaging from bezel 237. Spring lock 255 maintains a force on lock nut 254 to maintain it in the distal most position until the user backs off lock nut 254. When the user does so, levers 253 freely pivot about pins 258 so as to permit the user to disengage lips 253a from bezel 237, which in turn permits the user to detach clip 250 (and guide arm 230) from bezel 237 (and shaft 221).

Figure 10:
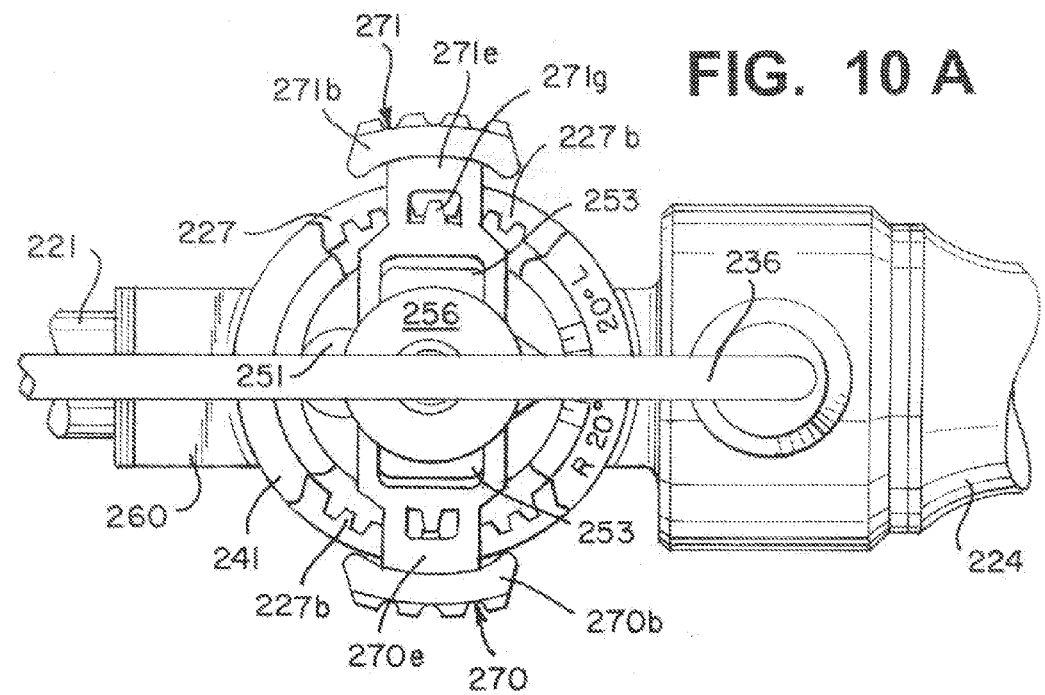
FIGS. 10A and 10B are, respectively, top and bottom plan views of the alignment guide of FIG. 6 at a first position, wherein the guide arm is co-planar with the shaft.
Figure 10:
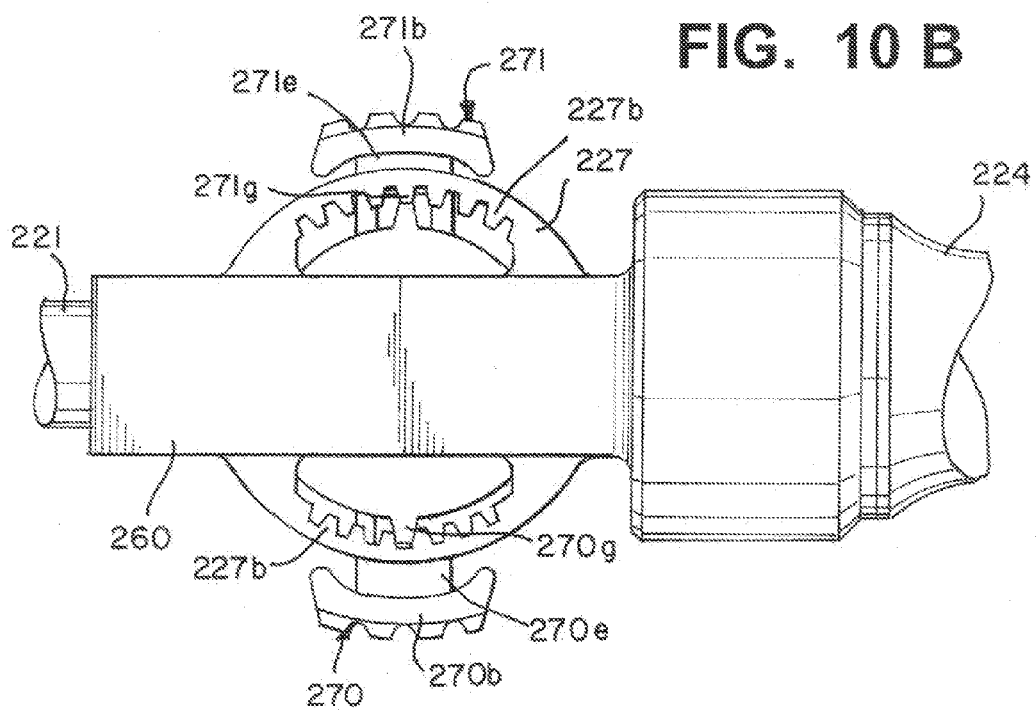

FIGS. 10A and 10B depict a detail top plan and bottom plan view of alignment guide 220 in a first position, wherein third portion 236 of guide arm 230 is aligned with the longitudinal axis A of shaft 221. Preferably, in this first position, guide arm 230 and shaft 221 are co-planar. Ratchet teeth 270g, 271g mate with base teeth 227b of ring 227a to prevent guide arm 230 from inadvertently moving relative to shaft 221. To rotate guide arm 230, the user applies a force to outer portions 270d, 271d to act against springs 274, which reduces the distance between the distal end of ratchet teeth 270g, 271g such that ratchet teeth 270c, 271c disengage from base teeth 227b. The user may then rotate bezel 237 and guide arm 230 with respect to the longitudinal axis A of shaft 221. FIGS. 11A-C depict a detailed top plan, bottom plan and perspective view of alignment guide 220 in a second position, wherein third portion 236 of guide arm 230 is not aligned with the longitudinal axis A of shaft 221.

Alignment guide 220 may be used in a surgical procedure to assist with correctly aligning surgical instruments. Referring to FIGS. 12-17, two methods of using alignment guide 20, 120, 220 are depicted. FIGS. 12-17 are schematic in that they do not show the cup or trial 40 that is attached to shaft 21 of guide 220 as being positioned within the prepared acetabulum, which in practice would be the case. Instead, they show the cup or trial 40 positioned just above the location of the prepared acetabulum. Other than the step of rotating the guide arm to set the anteversion angle, the method of using alignment guides 20, 120, 220 is the same regardless of which of the embodiments is used. As such, it is understood that, in the absence of language that indicates otherwise, reference to alignment guide 20, 120 or 220 and the elements of any one of those alignment guides applies equally to the other of those alignment guides.

Figure 12:
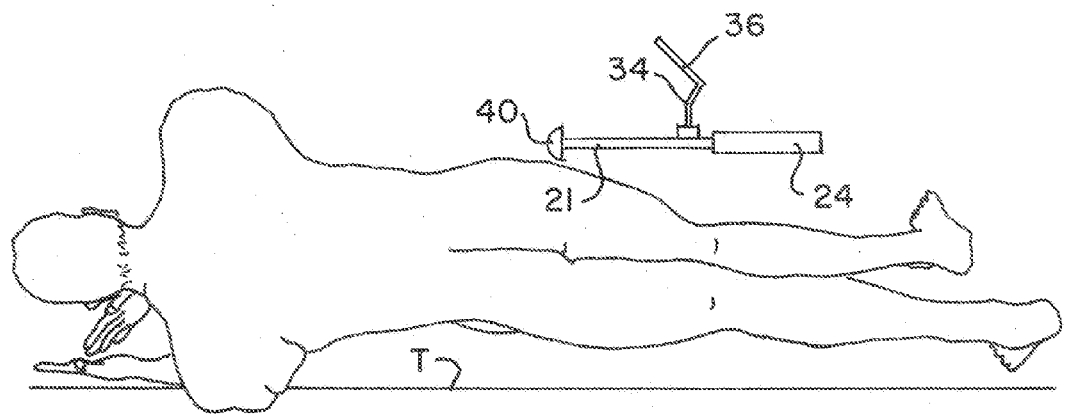
FIGS. 12A, 13A and 14A illustrate side elevational views of steps of a first method of using one of the first, second or third alignment guides of the present invention on a patient lying in a left lateral decubitus position.
FIGS. 12B, 13B and 14B illustrate plan views of the steps illustrated in FIGS. 12A, 13A and 14A, respectively.
Figure 12:
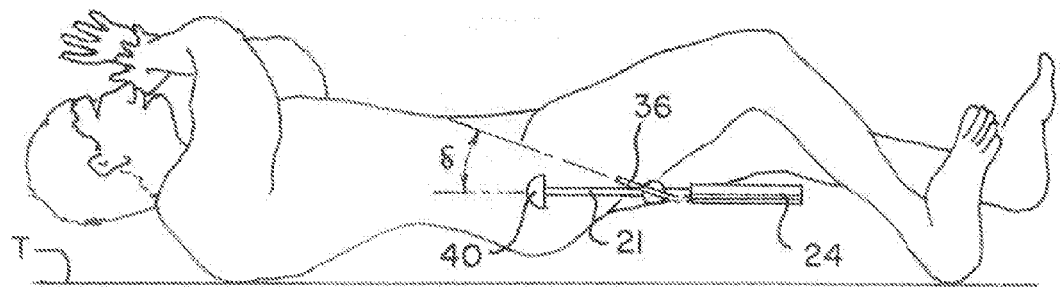
Figure 13:
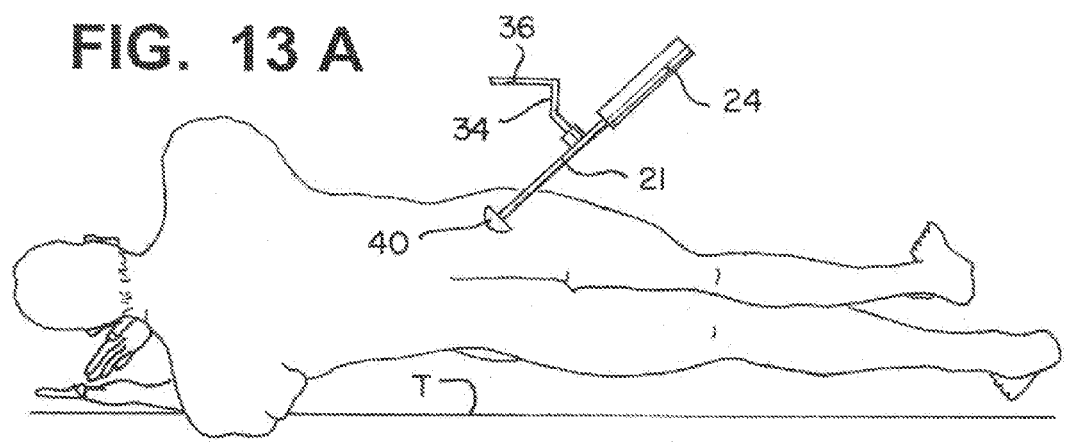
Figure 13:
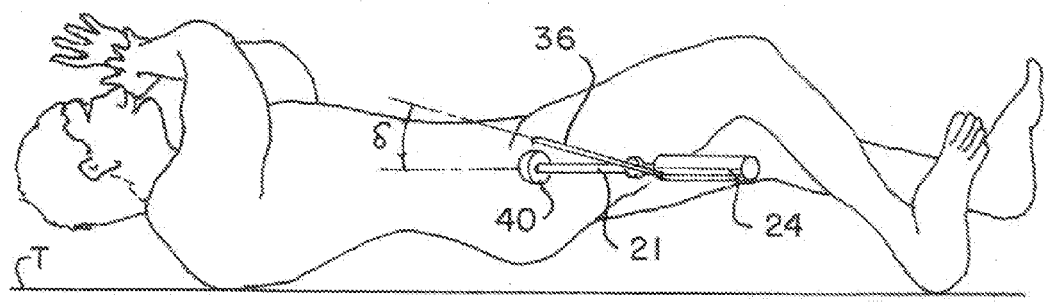
Figure 14:
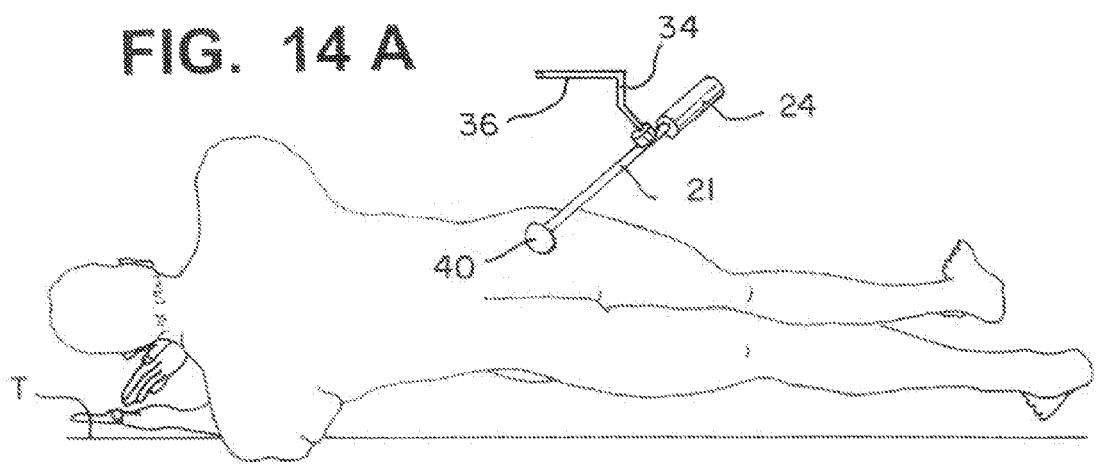
FIG. 14C illustrates a perspective plan view of the step illustrated in 14A and 14B.
Figure 14:
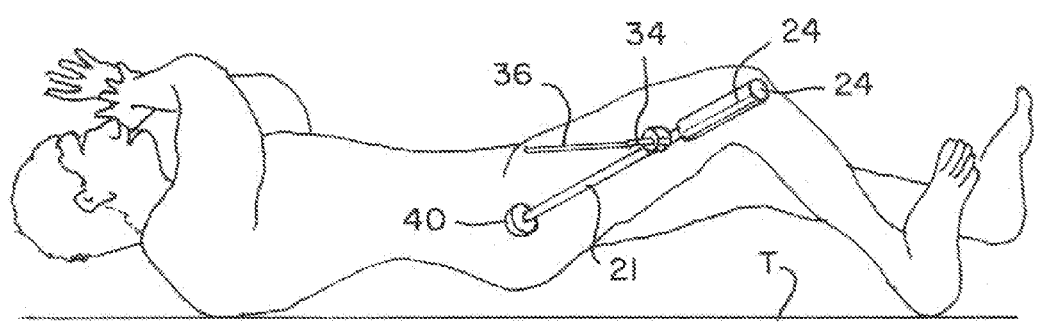
Figure 15:
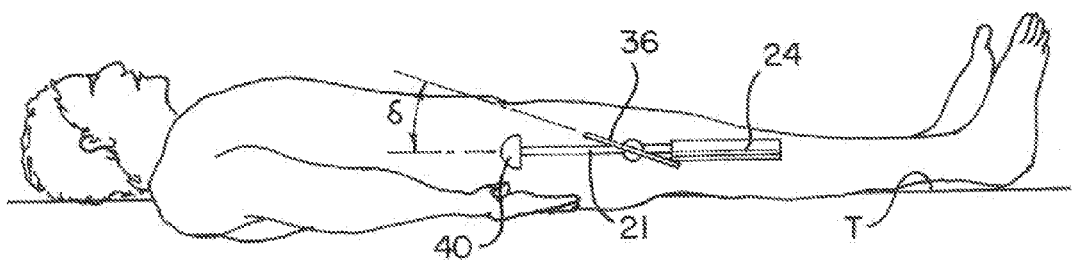
FIGS. 15A, 16A and 17A illustrate side elevational views of steps of a second method of using one of the first, second or third alignment guides of the present invention on a patient lying in a dorsal decubitus position.
FIGS. 15B, 16B and 17B illustrate plan views of the steps illustrated in FIGS. 15A, 16A and 17A, respectively.
Figure 14:
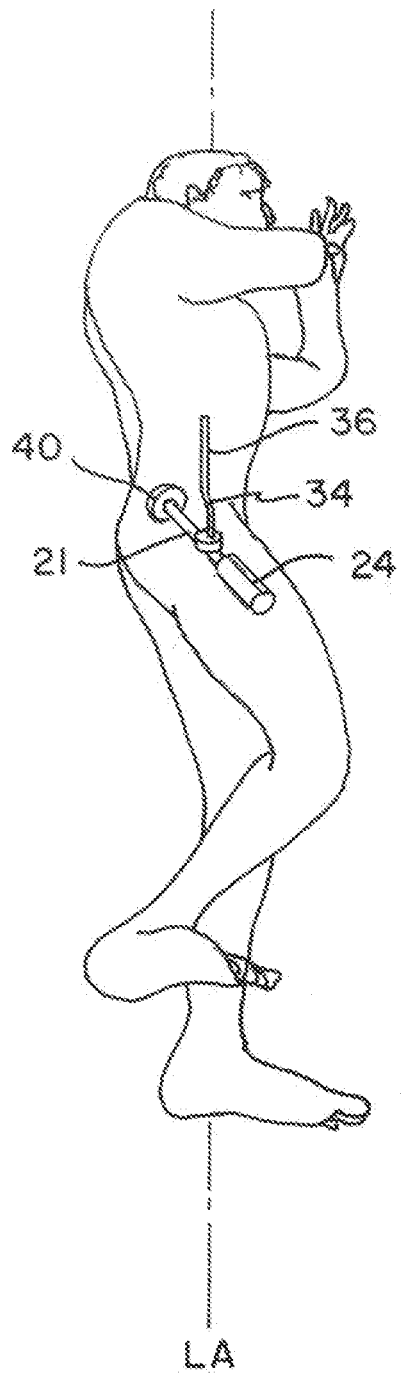
Figure 17:
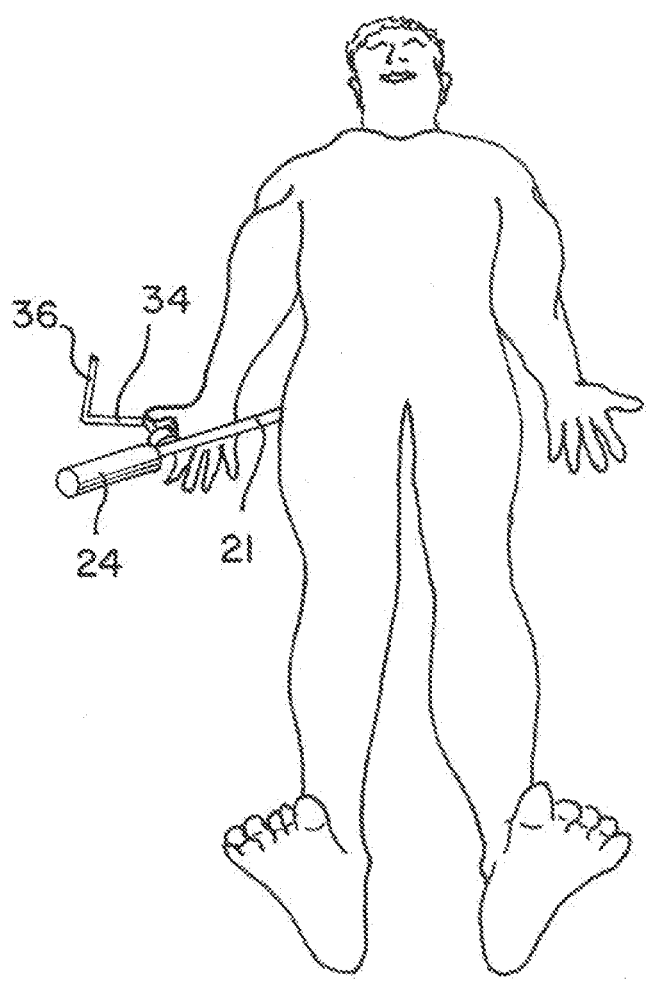
FIG. 17C illustrates a perspective plan view of the step illustrated in 17A and 17B.
Figure 15:
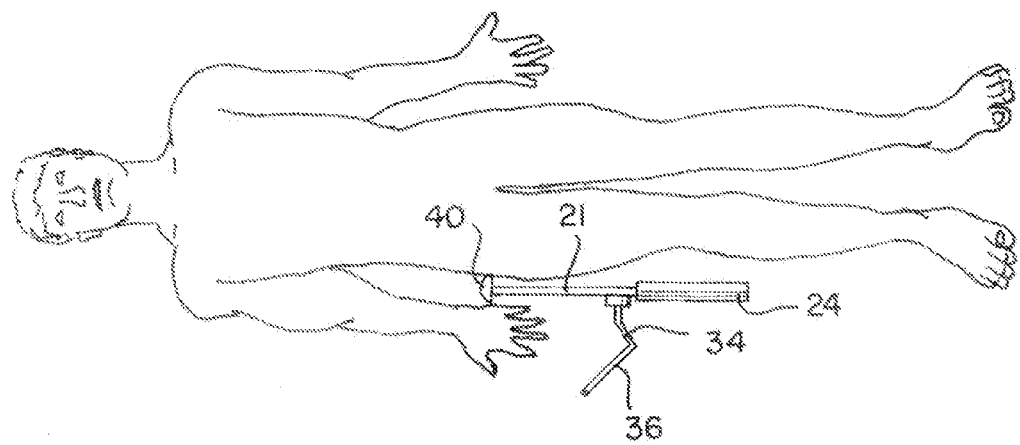
Figure 16:
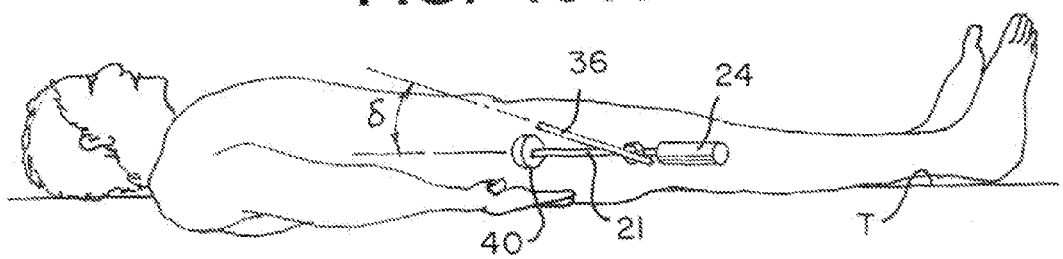
Figure 16:
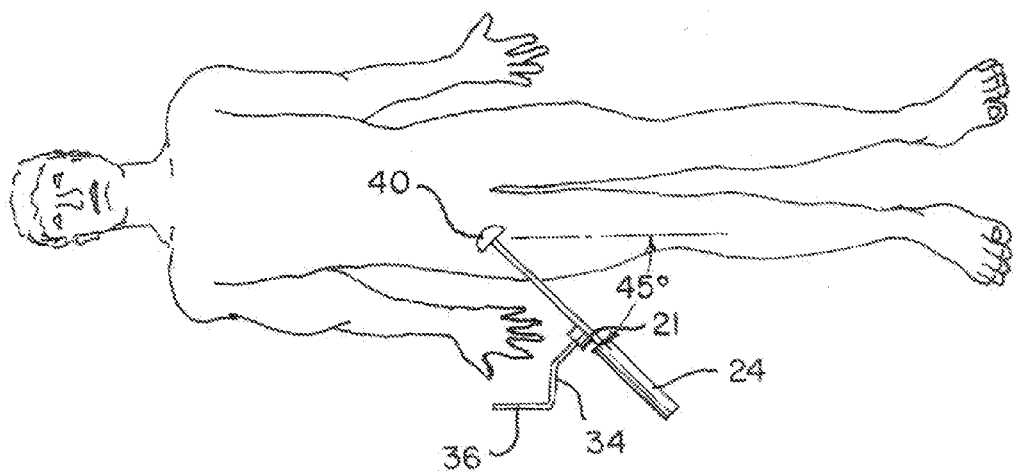
Figure 17:
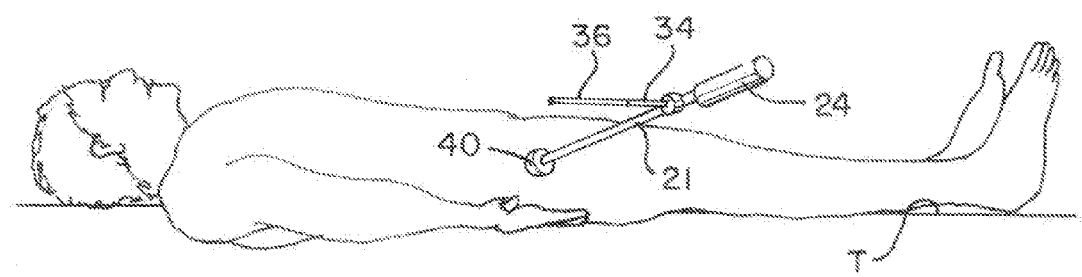
Figure 17:
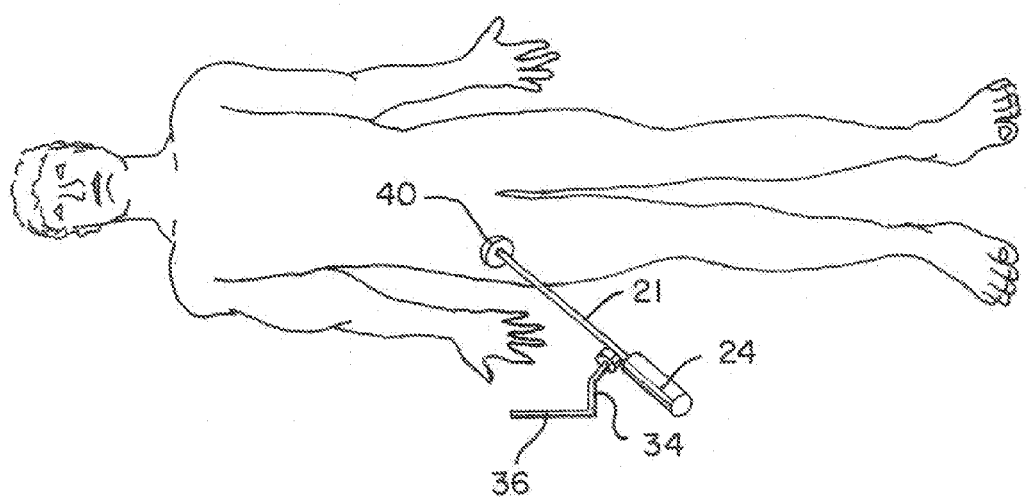

Alignment guide 20, 120, 220 helps to reduce misalignment of the implant and therefore helps to minimize wear of the implant. At the outset of the procedure, the patient is positioned on the operating table such that the patient is perpendicular to the table. In this way, the patient's pelvis is aligned such that it is vertical and not tilted with respect to the long (sagittal) axis of the body. The patient is typically constrained in one of two different ways to minimize movement during surgery. FIGS. 12-14 depict a first method of using alignment guides 20, 120, 220 on a patient lying on his left side in the left lateral decubitus position. FIGS. 15-17 depict a second method of using alignment guides 20, 120, 220 on a patient lying in the prone or dorsal decubitus position.

As a first surgical step, the surgeon accesses the joint via a series of incisions and dislocates the femur. The surgeon next uses a reamer to remove bone to form a hemispherical shape in the acetabulum. The reamed acetabulum enables a nearly unlimited number of angular cup positions as the cup may be seated at any angle within the hemisphere. As a result, there is no necessary correct orientation for an implanted cup.

Instead, the surgeon seeks to align the cup in a particular orientation so as to mate with the implanted femoral component of the hip system using his or her experience and local landmarks.

Referring to FIGS. 12-14, to align the trial or cup for seating within the acetabulum, the surgeon attaches the cup or trial 40 to alignment guide 20 at distal end 22 of shaft 21. Prior to positioning the cup or trial, guide arm 30 should be attached to shaft 21. If the surgeon/user is utilizing the simpler alignment guide embodiments 20, 120, referring to FIGS. 3-5, he or she simply engages the mating components 38, 39 of cover 37, 137 with the mating components 28, 29 of base 27, 127. To do so when using guide 220, and referring to FIGS. 6 and 7, the user ensures that lock nut 254 is backed off to the stop position (the underside of spring cap 256) to permit levers 253 of clip 250 to pivot with respect to one another. The user may then attach guide arm 230 to bezel 237. Clip 250 and bezel 237 are configured such that they can be assembled only in one orientation. Guide arm 230 is attached to shaft 221 by holding back levers 253 and inserting stakes 251a into guideholes 237g such that plate 251 is seated on the top surface of bezel 237. When clip 250 is held in this position, lips 253a engage at least the sides and preferably the underside of central bar 237b. At this stage, lock nut 254 is threaded down onto lower portion 252a of post 252 until the distal surface of lock nut 254 contacts a proximal surface of levers 253, thereby ensuring that levers 253 cannot pivot relative to bar 237b. In this position, guide arm 230 is secured to shaft 221.

At this point, the trial or acetabular implant 40 can be screwed onto the distal tip of the alignment guide, taking care not to damage the implant or the screw threads. The cup should be screwed on until tight against the shoulder in order to prevent damage to the threads and the cup during impaction.

Once the cup is assembled onto the alignment guide/inserter, when using alignment guide 220, the user may select the desired anteversion by rotating bezel 237. To do so, as described above, with reference to FIGS. 6 and 7, the user presses on the opposed grip surfaces 270h, 271h of ratchet members 270, 271, which disengage ratchet teeth 270c, 271c from base teeth 227b. The user may rotate bezel 237 freely and the bezel to the desired anteversion. Anteversion is most preferably available in 5 degree increments between 0 and 35 degrees. The user needs to take care to ensure that the correct version is used as determined by the hip that is being operated upon; i.e. the left or right hip. Once the desired anteversion is achieved, the user releases grip surfaces 270h, 271h to re-engage ratchet teeth 270c, 271c with base teeth 227b.

If the surgeon/user is utilizing the simpler alignment guide embodiments 20, 120, referring to FIGS. 3-5, he or she simply disengages either cover 37, 137 from base 27, 127, and rotates cover 37, 137 with respect to shaft 21, 121. Once the desired anteversion is achieved cover 37, 137 is re-engaged with base 27, 127 by mating the protrusions and tabs with their corresponding recesses and slots.

The user next positions the alignment guide 20, 120, 220 so as to locate the acetabular component in the prepared acetabulum. FIGS. 12-14 schematically depict a first method of using one of the first, second or third alignment guides 20, 120, 220 on a patient lying on his left side in a left lateral decubitus position. FIG. 12A depicts a side elevational view and FIG. 12B depicts the corresponding top plan view of a first step of a preferred method, wherein the user holds the cup or trial 40 in the prepared acetabulum and uses alignment guide 20 to position the cup in a pre-planned orientation. Once in the pre-planned orientation, the user may modify that orientation depending on how the cup is aligned with respect to how the implant fits with the patient using, for example, the patient's anatomic landmarks (such as the transverse acetabular ligament, bilateral anterosuperior iliac spines, the acetabular labrum and the upper margin of the pubic symphysis) or other factors specific to the patient.

As depicted in FIGS. 12A and 12B, the user positions alignment guide 20 using handle 24 such that shaft 21 is substantially parallel to horizontal (defined as being the level of the operating table, designated as T) and in line with the long axis of the patient. Note that portion 36 has been rotated (or anteverted) with respect to shaft 21 to an angle designated as $\delta$. As described, above angle $\delta$ is typically between 0 and 35 degrees. As shown, angle $\delta$ is approximately 20 degrees. One skilled in the art will recognize that guide arm 30 need not be rotated at the outset of the method, but could be adjusted at any time during the method and may be adjusted more than once depending upon the surgeon's preference or need to refine the ultimate location of the trial or cup.

Next, referring to FIGS. 13A and 13B, the user, while maintaining the position of cup or trial 40 relative to the patient's prepared acetabulum, grasps handle 24 and sets the inclination angle by moving handle 24 toward the head of the patient or anteriorly. In doing so, the shaft 21 is pivoted about a fixed point in the acetabulum until portion 36 of guide arm 30 is substantially parallel to the operating table when viewed from the side of the table (as depicted in the side elevational view of FIG. 13A). Typically, the inclination angle is between 35 and 55 degrees, and preferably 45 degrees, as is depicted in FIG. 13A.

Referring to FIGS. 14A, 14B and 14C, the user next sets the anteversion angle and positions the alignment guide in its final position. As with the prior two sets of figures, FIGS. 14A and 14B are respectively side elevational and top plan views of alignment guide 20 positioned in the final position. FIG. 14C is a perspective view of the patient with the alignment guide in the final position. In transitioning the alignment guide from the position depicted in the prior set of figures, while maintaining the position of cup or trial 40 relative to the patient's prepared acetabulum, the user grasps handle 24 and anteverts handle 24. That is, the user moves handle 24 toward the front or anterior of the patient. In doing so, the shaft 21 is pivoted about a fixed point in the acetabulum until portion 36 of guide arm 30 is substantially parallel to the operating table when viewed from the side of the table (as depicted in the side elevational view of FIG. 14A) and is substantially parallel to the long axis LA of the patient (as viewed in the top plan view of FIGS. 14B and 14C). In order to achieve the position of being substantially parallel to both the long axis of the patient and the operating table, the user must drop proximal end of handle 24 medially toward the patient's body as handle 24 is pivoted anteriorly. This motion ensures that the user closes down the inclination angle while anteverting the cup such that the operative inclination angle as viewed from the side elevational view substantially matches the sought radiographic inclination angle.

FIGS. 15-17 depict a second method of using alignment guides 20, 120, 220 on a patient lying in the prone or dorsal decubitus position. FIG. 15A depicts a side elevational view and FIG. 15B depicts the corresponding top plan view of a first step of a second preferred method, wherein the user holds the cup or trial 40 in the prepared acetabulum and uses alignment guide 20 to position the cup in a pre-planned orientation. Once in the pre-planned orientation, the user may modify that orientation depending on how the cup is aligned with respect to how the implant fits with the patient using, for example, the patient's anatomic landmarks or other factors specific to the patient.

As depicted in FIGS. 15A and 15B, the user positions alignment guide 20 using handle 24 such that shaft 21 is substantially parallel to horizontal (defined as being the level of the operating table, designated as T) and in line with the long axis of the patient. Note that portion 36 has been rotated (or anteverted) with respect to shaft 21 to an angle designated as δ. As described, above angle δ is typically between 0 and 35 degrees. As shown, angle δ is approximately 20 degrees. One skilled in the art will recognize that guide arm 30 need not be rotated at the outset of the method, but could be adjusted at any time during the method and may be adjusted more than once depending upon the surgeon's preference or need to refine the ultimate location of the trial or cup.

Next, referring to FIGS. 16A and 16B, the user, while maintaining the position of cup or trial 40 relative to the patient's prepared acetabulum, grasps handle 24 and sets the inclination angle by moving handle 24 toward the head of the patient or anteriorly. In doing so, the shaft 21 is pivoted about a fixed point in the acetabulum until portion 36 of guide arm 30 is substantially parallel to the long axis of the patient when viewed from the top of the table (as depicted in the top plan view of FIG. 16B). Typically, the inclination angle is between 35 and 55 degrees, and preferably 45 degrees, as is depicted in FIG. 16B.

Referring to FIGS. 17A, 17B and 17C, the user next sets the anteversion angle and positions the alignment guide in its final position. As with the prior two sets of figures, FIGS. 17A and 17B are respectively side elevational and top plan views of the alignment guide 20 positioned in the final position. FIG. 17C is a perspective view of the patient with the alignment guide in the final position. In transitioning the alignment guide from the position depicted in the prior set of figures, while maintaining the position of cup or trial 40 relative to the patient's prepared acetabulum, the user grasps handle 24 and anteverts handle 24. That is, the user moves handle 24 toward the front or anterior of the patient. In doing so, the shaft 21 is pivoted about a fixed point in the acetabulum until portion 36 of guide arm 30 is substantially parallel to the operating table when viewed from the side of the table (as depicted in the side elevational view of FIG. 17A) and is substantially parallel to the long axis LA of the patient (as viewed in the top plan view of FIGS. 17B and 17C). In order to achieve the position of being substantially parallel to both the long axis of the patient and the operating table, the user must drop proximal end of handle 24 medially toward the patient's body as handle 24 is pivoted anteriorly. This motion ensures that the user closes down the inclination angle while anteverting the cup such that the operative inclination angle as viewed from the side elevational view substantially matches the sought radiographic inclination angle.

As described above, the user may choose to estimate the how much he or she wants to antevert the guide arm and adjust it prior to surgery or adjust for anteversion while orienting the alignment guide and/or trialing the cup component. While the above methods of using alignment guide 20 are described (and shown) as separate distinct steps for purposes of illustration, it is understood that one skilled in the art can adjust for version or inclination using separate steps or simply align portion 36 such that it is both substantially parallel to the operating table when viewed from the side of the table (in the side elevational view) and is substantially parallel to the long axis LA of the patient when viewed from above the table (in the top plan view).

Once alignment guide 20 is in its final position, the user checks local landmarks proximate the acetabulum to ensure that the cup is located in a satisfactory position. Once a satisfactory position is achieved, the user impacts the acetabular component into position using the alignment guide/inserter. Prior to doing so, it is recommended that guide arm 30 be detached from shaft 21.

Further modifications to, and applications of, the present invention will be readily apparent to the skilled person from the teaching herein, without departing from the scope of the appended claims.

The invention claimed is:

1. A method of aligning an alignment guide relative to a reamed acetabulum of a patient, the patient being positioned on an operating table and having a long axis, comprising the steps of:
   manipulating an alignment guide comprising a shaft having a longitudinal axis, a distal end, a guide arm having a housing, a first portion, a second portion and a third portion, the first portion attached to the housing and extending therefrom along a first axis substantially perpendicular to the longitudinal axis, the second portion extending from the first portion at a first predetermined angle along a second axis, and the third portion extending from the second portion at a second predetermined angle;
   attaching a cup or trial to the distal end of the shaft;
   contacting the cup or trial with the reamed acetabulum;
   while maintaining contact between the cup or trial and the reamed acetabulum, adjusting the position of the alignment guide such that the third portion of the guide arm i) is substantially parallel to the top surface of the operating table, when viewed from the side of the table, and ii) is substantially parallel to the long axis of the patient; and
   wherein as the position of the alignment guide is rotated to correct for the version angle, the inclination angle is maintained; and
   wherein the housing includes a base attached to the shaft, and a plate rotatable about the first axis relative to the base, the first portion being attached to the plate and the base has an inner surface, and further comprising a ratchet disposed at least partially within the base, the ratchet configured to act against the inner surface of the base, the ratchet including a first ratchet portion having a first outer surface configured to act against the inner surface of the base, a second ratchet portion having a second outer surface configured to act against the inner surface of the base, and at least one spring disposed between the first ratchet portion and the second ratchet portion and wherein the first ratchet portion has an inner surface and a pin extending from the inner surface configured to be attached to the at least one spring.

2. The method of claim 1, wherein the guide arm is attachable to the shaft and comprising the step of attaching the guide arm to the shaft.

3. The method of claim 2, wherein the guide arm and shaft have respective mating components and the attaching step comprises the steps of engaging the mating components of the guide arm with the mating components of the shaft.

4. The method of claim 1, wherein the adjusting step comprises the step of positioning the alignment guide such that the shaft is substantially parallel to the operating table and substantially parallel with the long axis of the patient.

5. The method of claim 1, wherein the adjusting step comprises the step of moving a proximal end of the shaft anteriorly until the third portion of the guide arm is substantially parallel to the operating table when viewed from the side of the table.

6. The method of claim 1, wherein the guide arm is rotatable about the first axis, and is rotated from a first position to a second position of between 0 and 35 degrees relative to the longitudinal axis.

7. The method of claim 1, further comprising the step of surgically accessing the patient's acetabulum, and wherein the rotating step is performed after the accessing step.

8. A method of aligning an alignment guide relative to a reamed acetabulum of a patient positioned on an operating table, the patient being positioned on an operating table and having a long axis, comprising the steps of:
manipulating an alignment guide comprising a shaft having a longitudinal axis and a distal end; a housing attached to the shaft and being rotatable about a first axis substantially perpendicular to the longitudinal axis; a guide arm having a first portion and a second portion, the first portion being attached to the housing and extending from the housing along a second axis, the second portion extending from the first portion at a first predetermined angle;
attaching a cup or trial to the distal end of the shaft;
while maintaining the position of the distal end of the shaft relative to the first axis, rotating the guide arm from a first position about the first axis relative to the shaft to a second position, whereat the second portion defines an angle of between 0 and 35 degrees with the longitudinal axis of the shaft; and
adjusting the position of the alignment guide such that the second portion of the guide arm i) is substantially parallel to the top surface of the operating table, when viewed from the side of the table, and ii) is substantially parallel to the long axis of the patient, and wherein as the position of the alignment guide is rotated to correct for the version angle, the inclination angle is maintained;
wherein the housing includes a base attached to the shaft, and a plate rotatable about the first axis relative to the base, the first portion being attached to the plate and the base has an inner surface, and further comprising a ratchet disposed at least partially within the base, the ratchet configured to act against the inner surface of the base, the ratchet including a first ratchet portion having a first outer surface configured to act against the inner surface of the base, a second ratchet portion having a second outer surface configured to act against the inner surface of the base, and at least one spring disposed between the first ratchet portion and the second ratchet portion and wherein the first ratchet portion has an inner surface and a pin extending from the inner surface configured to be attached to the at least one spring.

9. The method of claim 8, wherein the guide arm is attachable to the shaft and comprising the step of attaching the guide arm to the shaft.

10. The method of claim 9, wherein the guide arm and shaft have respective mating components and the attaching step comprises the steps of engaging the mating components of the guide arm with the mating components of the shaft.

11. The method of claim 8, further comprising the step of:
contacting the cup or trial with the reamed acetabulum.

12. The method of claim 11, wherein the contacting step comprises the step of locating the cup or trial within the reamed acetabulum.

13. The method of claim 11, wherein the adjusting step comprises the step of positioning the alignment guide such that the shaft is substantially parallel to the operating table and substantially parallel with the long axis of the patient.

14. The method of claim 11, wherein the adjusting step comprises the step of moving the proximal end of the shaft anteriorly until the second portion of the guide arm is substantially parallel to the operating table when viewed from the side of the table.

15. The method of claim 8, wherein the guide arm is rotated to a second position of approximately 20 degrees.

16. The method of claim 8, further comprising the step of surgically accessing the patient's acetabulum, and wherein the rotating step is performed after the accessing step.

17. A method of aligning an alignment guide relative to a reamed acetabulum of a patient positioned on an operating table, the patient being positioned on an operating table and having a long axis, comprising the steps of:
manipulating an alignment guide comprising a shaft having a longitudinal axis; a housing attached to the shaft; a guide arm having a first portion, a second portion and third portion, the first portion being at least partially received in the housing and extending from the housing along a first axis that is substantially perpendicular to the longitudinal axis, the second portion extending from the first portion at a first predetermined angle, the third portion extending from the second portion at a second predetermined angle, the third portion defining an angle of approximately 20 degrees with the longitudinal axis;
attaching a cup or trial to the distal end of the shaft; and
while maintaining the position of the distal end of the shaft relative to the first axis, adjusting the position of the alignment guide such that the third portion of the guide arm i) is substantially parallel to the top surface of the operating table, when viewed from the side of the table, and ii) is substantially parallel to the long axis of the patient, and wherein as the position of the alignment guide is rotated to correct for the version angle, the inclination angle is maintained;
wherein the housing includes a base attached to the shaft, and a plate rotatable about the first axis relative to the base, the first portion being attached to the plate and the base has an inner surface, and further comprising a ratchet disposed at least partially within the base, the ratchet configured to act against the inner surface of the base, the ratchet including a first ratchet portion having a first outer surface configured to act against the inner surface of the base, a second ratchet portion having a second outer surface configured to act against the inner surface of the base, and at least one spring disposed between the first ratchet portion and the second ratchet portion and wherein the first ratchet portion has an inner surface and a pin extending from the inner surface configured to be attached to the at least one spring.

18. The method of claim 17, further comprising the step of:
contacting the cup or trial with the reamed acetabulum.

19. The method of claim 18, wherein the contacting step comprises the step of locating the cup or trial within the reamed acetabulum.

* * * * *